United States Patent
Siegel et al.

(10) Patent No.: US 8,664,246 B2
(45) Date of Patent: Mar. 4, 2014

(54) SUBSTITUTED PYRIDINES, AND USE THEREOF AS GSK3 INHIBITORS

(75) Inventors: Stephan Siegel, Berlin (DE); Andreas Wilmen, Köln (DE); Niels Svenstrup, Velbert (DE); Mark Jean Gnoth, Mettmann (DE); Adrian Tersteegen, Wuppertal (DE); Ulrich Rester, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 80 days.

(21) Appl. No.: 13/056,676

(22) PCT Filed: Jul. 21, 2009

(86) PCT No.: PCT/EP2009/005266
§ 371 (c)(1),
(2), (4) Date: Apr. 18, 2011

(87) PCT Pub. No.: WO2010/012398
PCT Pub. Date: Feb. 4, 2010

(65) Prior Publication Data
US 2011/0190316 A1    Aug. 4, 2011

(30) Foreign Application Priority Data
Jul. 30, 2008   (DE) .......................... 10 2008 035 552

(51) Int. Cl.
*A61K 31/4545* (2006.01)
*C07D 401/12* (2006.01)

(52) U.S. Cl.
USPC ........... 514/318; 514/255; 544/360; 546/193; 546/194

(58) Field of Classification Search
USPC ............ 514/255, 318; 544/360; 546/193, 194
See application file for complete search history.

(56) References Cited

U.S. PATENT DOCUMENTS 6,417,185 B1 * 7/2002 Goff et al. .................. 514/235.8
7,045,519 B2 * 5/2006 Nuss et al. .................. 514/235.8

FOREIGN PATENT DOCUMENTS

WO    WO2004742278    *    9/2004

OTHER PUBLICATIONS

Braga et al. "Making crystal from . . . " roy Chem. Soc. Chem. Commun. p. 3635-3645 (2005).*
Chemcats 0102817838 (2012).*
Chen et al. "Preparation of hetero . . . " CA137:201332 (2002).*
Colghlan et al. "Seletive small . . . " Chem. & Biol. v.7(10) p. 793-803 (2000).*
Meijer et al. "PHarmacological inhibitors . . . " Trends in Phar. Sci. v.25(9) 471-480 (2004).*
Dorwald "Side reactions in organic . . . " p. ix (2005).*
Seddon "Pseudopolymorph . . . " Cry. Growth & design. v.4(6) p. 1087 (2004).*
Uto "Piperidine . . . " Exp. Opin. ther. Patent 22(1) 89-93 (2011).*
Zhang et al. "Design synthesis . . . " Eur. J. med. Chem. xxx p. 1-9 (2012).*
Improper Markush p. 1, 64-67 (2011).*

* cited by examiner

*Primary Examiner* — Celia Chang

(57) ABSTRACT

The invention relates to substituted pyridines and to processes for preparation thereof, and to the use thereof for production of medicaments for treatment and/or prophylaxis of diseases, especially of haematological disorders, preferably of leukopenia and neutropenia.

8 Claims, No Drawings

SUBSTITUTED PYRIDINES, AND USE THEREOF AS GSK3 INHIBITORS

This application is a National Stage Application, filed under 35 U.S.C. §371, based on International Application Number PCT/EP2009/005266, filed Jul. 21, 2009, which claims priority to German Patent Application Number 102008035552.6, filed on Jul. 30, 2008.

The invention relates to substituted pyridines and to processes for preparation thereof, and to the use thereof for production of medicaments for treatment and/or prophylaxis of diseases, especially of haematological disorders, preferably of leukopenia and neutropenia.

Glycogen synthase kinase 3 (GSK3) belongs to the family of the serine/threonine kinases. Specific substrates include cytoskeletal proteins and transcription factors. Two isoforms, GSK3α and GSK3β, have been identified to date (Woodgett J R., Trends Biochem. Sci. (1991), 16(5), 177-81). Both isoforms are constitutively active in principally resting, nonproliferative cells.

GSK3β is of central significance within the Wnt/wingless signal transduction pathway. This pathway is one of the most important evolutionarily conserved signalling systems. Wnt signals control very early patterning processes during embryogenesis, they induce mesoderm formation and many organs, and they control the proliferation and differentiation of stem cells (Wodarz A., Nusse R., Annu. Rev. Cell Dev. Biol. (1998), 14, 59-88; Kirstetter et al., Nat Immunol. (2006), 7(10), 1048-56). There is intracellular compartmentalization of the Wnt signalling pathway, which makes it possible to control a wide variety of different processes. Within the Wnt cascade, glycogen synthase kinase 3 forms part of a multiprotein complex which includes the structural molecules axin, the tumour suppressor protein APC and the transcription cofactor β-catenin. β-Catenin is the most important substrate of GSK3β. The consequence of this GSK3β-mediated phosphorylation is the proteasomal degradation of β-catenin. Inhibition of GSK3 activity leads to an accumulation of β-catenin in the cell with subsequent translocation into the cell nucleus. β-Catenin acts therein as a cofactor in transcription complexes and thus is partly responsible for the expression of defined target genes.

Radiotherapies or chemotherapies are among the standard approaches to controlling cancer. Both forms of therapy are nonspecific in relation to their target cells, i.e. not only tumour cells but also untransformed proliferating cells are affected. These untransformed proliferating cells also include haematopoietic progenitor cells which develop to become neutrophilic granulocytes inter alia. A significant reduction in the number of neutrophils is referred to as neutropenia. The clinical result of a neutropenia induced by chemotherapy or radiotherapy is an increased susceptibility to infection. If the neutropenia is substantial there is an increase in the morbidity and, in some circumstances, also the mortality of a therapy (O'Brien et al., British Journal of Cancer (2006), 95, 1632-1636).

Inhibition of GSK3 activity leads to an increased rate of proliferation and differentiation of haematopoietic stem cells and can accordingly be utilized for therapeutic intervention in relation to a therapy-induced neutropenia.

WO 99/65897 and WO 02/20495 describe inter alia pyridines as glycogen synthase kinase 3 (GSK3) inhibitors for treatment of diabetes, cancer and disorders of the central nervous system. WO 2003/049739 describes pyrimidines as glycogen synthase kinase 3 (GSK3) inhibitors for treatment of diabetes, cancer and disorders of the central nervous system.

It is therefore an object of the present invention to provide novel compounds as GSK3β inhibitors for treatment of haematological disorders, preferably of neutropenia in humans and animals.

The invention provides compounds of the formula

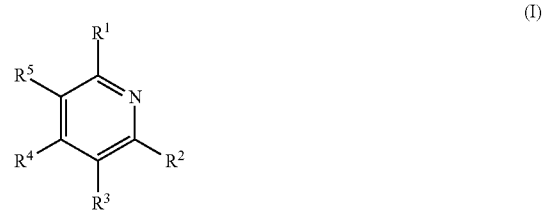

in which
$R^1$ is a group of the formula

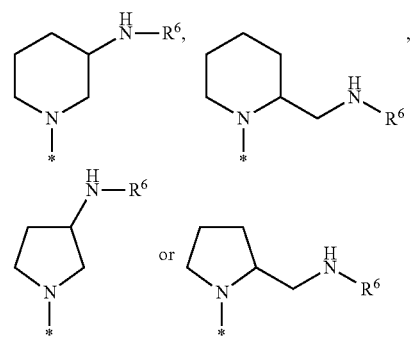

where
* is the attachment site to the heterocycle,
$R^6$ is pyrid-2-yl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,2-pyrazol-5-yl,
  where pyrid-2-yl, pyrimid-2-yl, 1,3-thiazol-2-yl and 1,3-thiazol-4-yl are substituted by 1 to 2 substituents, where the substituents are each independently selected from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl,
  in which alkyl, alkylamino, alkylcarbonyl, alkylaminocarbonyl and cycloalkylcarbonyl may be substituted by one substituent, where the substituent is selected from the group consisting of halogen, cyano, hydroxyl, amino, trifluoromethyl and $C_3$-$C_6$-cycloalkyl,
  and
  where 2-aminopyrimid-4-yl, 2-cyclopropylaminopyrimid-4-yl, 2-methylaminopyrimid-4-yl, 2-ethylaminopyrimid-4-yl and 1,2-pyrazol-5-yl may each be substituted by 1 to 2 substituents, where the substituents are each independently selected from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$- alkoxycarbonyl, $C_1$-$C_4$-alkylaminocarbonyl and $C_3$-$C_6$-cycloalkylcarbonyl, $R^2$ is phenyl,
where phenyl may be substituted by 1 to 3 substituents, where the substituents are each independently selected from the group consisting of hydroxyl, halogen, cyano, trifluoromethyl, trifluoromethoxy, aminocarbonyl, $C_1$-$C_4$-alkyl, $C_1$-$C_4$-alkoxy, $C_1$-$C_4$-alkylamino, $C_1$-$C_4$-alkoxymethyl, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulphonyl, $C_1$-$C_4$-alkylsulphonylamino, $C_1$-$C_4$-alkylaminosulphonyl, phenyl, pyrrolidinyl, piperidinyl, morpholinyl, piperazinyl, pyrrolidinylmethyl, piperidinylmethyl, morpholinylmethyl and piperazinylmethyl,
in which phenyl, pyrrolidinyl, piperidinyl, morpholinyl, piperazinyl, pyrrolidinylmethyl, piperidinylmethyl, morpholinylmethyl and piperazinylmethyl may each be substituted by 1 to 3 substituents, where the substituents are each independently selected from the group consisting of halogen, cyano, trifluoromethyl, trifluoromethoxy and $C_1$-$C_4$-alkyl, $R^3$ is hydrogen, halogen, cyano, trifluoromethyl, $C_1$-$C_3$-alkyl or cyclopropyl, either $R^4$ is hydrogen, halogen, cyano, trifluoromethyl, $C_1$-$C_3$-alkyl or cyclopropyl, and $R^5$ is halogen, cyano, trifluoromethyl, hydroxycarbonyl, aminocarbonyl, $C_1$-$C_4$-alkyl, $C_1$-$C_4$-alkoxycarbonyl, $C_1$-$C_4$-alkylaminocarbonyl or 5- or 6-membered heterocyclylcarbonyl,
where heterocyclylcarbonyl may be substituted by 1 to 3 substituents, where the substituents are each independently selected from the group consisting of oxo, halogen, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
and
where alkylaminocarbonyl may be substituted by one substituent, where the substituent is selected from the group consisting of hydroxyl, amino, hydroxycarbonyl, aminocarbonyl, $C_1$-$C_4$-alkoxy, $C_1$-$C_4$-alkylamino and 5- or 6-membered heterocyclyl,
in which heterocyclyl may be substituted by 1 to 2 substituents, where the substituents are each independently selected from the group consisting of oxo, halogen, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, or $R^4$ is halogen, cyano, trifluoromethyl, hydroxycarbonyl, aminocarbonyl, $C_1$-$C_4$-alkyl, $C_1$-$C_4$-alkoxycarbonyl, $C_1$-$C_4$-alkylaminocarbonyl or 5- or 6-membered heterocyclylcarbonyl,
where heterocyclylcarbonyl may be substituted by 1 to 3 substituents, where the substituents are each independently selected from the group consisting of oxo, halogen, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
and
where alkylaminocarbonyl may be substituted by one substituent, where the substituent is selected from the group consisting of hydroxyl, amino, hydroxycarbonyl, aminocarbonyl, $C_1$-$C_4$-alkoxy, $C_1$-$C_4$-alkylamino and 5- or 6-membered heterocyclyl,
in which heterocyclyl may be substituted by 1 to 2 substituents, where the substituents are each independently selected from the group consisting of oxo, halogen, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, and $R^5$ is hydrogen, halogen, cyano, trifluoromethyl, $C_1$-$C_3$-alkyl or cyclopropyl, and the salts thereof, solvates thereof and the solvates of the salts thereof.

Inventive compounds are the compounds of the formula (I) and the salts, solvates and solvates of the salts thereof, and also the compounds encompassed by formula (I) and specified hereinafter as working example(s), and the salts, solvates and solvates of the salts thereof, to the extent that the compounds encompassed by formula (I) and specified hereinafter are not already salts, solvates and solvates of the salts.

Depending on their structure, the inventive compounds may exist in stereoisomeric forms (enantiomers, diastereomers). The invention therefore encompasses the enantiomers or diastereomers and the respective mixtures thereof. The stereoisomerically homogeneous constituents can be isolated from such mixtures of enantiomers and/or diastereomers in a known manner.

If the inventive compounds can occur in tautomeric forms, the present invention encompasses all tautomeric forms.

In the context of the present invention, preferred salts are physiologically acceptable salts of the inventive compounds. The invention also encompasses salts which themselves are unsuitable for pharmaceutical applications but which can be used, for example, for the isolation or purification of the inventive compounds.

Physiologically acceptable salts of the inventive compounds include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of customary bases, preferred examples being alkali metal salts (e.g. sodium salts and potassium salts), alkaline earth metal salts (e.g. calcium salts and magnesium salts) and ammonium salts, derived from ammonia or organic amines having 1 to 16 carbon atoms, preferred examples being ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

In the context of the invention, solvates refer to those forms of the inventive compounds which, in the solid or liquid state, form a complex by coordination with solvent molecules. Hydrates are a specific form of the solvates in which the coordination is with water.

Moreover, the present invention also encompasses prodrugs of the inventive compounds. The term "prodrugs" includes compounds which may themselves be biologically active or inactive but are converted to inventive compounds while resident in the body (for example metabolically or hydrolytically).

In the context of the present invention, unless specified otherwise, the substituents are defined as follows:

Alkyl per se and "Alk" and "alkyl" in alkoxy, alkylamino, alkylcarbonyl, alkoxycarbonyl, alkylaminocarbonyl, alkylcarbonylamino, alkylsulphonyl, alkylsulphonylamino and alkylaminosulphonyl is a linear or branched alkyl radical having 1 to 4 carbon atoms, preferred examples being methyl, ethyl, n-propyl, isopropyl, n-butyl and tert-butyl.

For example and with preference, alkoxy is methoxy, ethoxy, n-propoxy, isopropoxy, n-butoxy and tert-butoxy.

Alkylamino is an alkylamino radical having one or two (independently selected) alkyl substituents, preferred examples being methylamino, ethylamino, n-propylamino, isopropylamino, tert-butylamino, N,N-dimethylamino, N,N-diethylamino, N-ethyl-N-methylamino, N-methyl-N-n-propylamino, N-isopropyl-N-n-propylamino and N-tert-butyl-N-methylamino. $C_1$-$C_4$-Alkylamino is, for example, a monoalkylamino radical having 1 to 4 carbon atoms or a dialkylamino radical having in each case 1 to 4 carbon atoms per alkyl substituent.

For example and with preference, alkylcarbonyl is methylcarbonyl, ethylcarbonyl, n-propylcarbonyl, isopropylcarbonyl, n-butylcarbonyl and tert-butylcarbonyl.

For example and with preference, alkoxycarbonyl is methoxycarbonyl, ethoxycarbonyl, n-propoxycarbonyl, isopropoxycarbonyl, n-butoxycarbonyl and tert-butoxycarbonyl.

Alkylaminocarbonyl is an alkylaminocarbonyl radical having one or two (independently selected) alkyl substituents, for example and with preference methylaminocarbonyl, ethylaminocarbonyl, n-propylaminocarbonyl, isopropylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl and N-tert-butyl-N-methylaminocarbonyl. $C_1$-$C_4$-Alkylaminocarbonyl is, for example, a monoalkylaminocarbonyl radical having 1 to 4 carbon atoms or a dialkylaminocarbonyl radical having in each case 1 to 4 carbon atoms per alkyl substituent.

For example and with preference, alkylcarbonylamino is methylcarbonylamino, ethylcarbonylamino, n-propylcarbonylamino, isopropylcarbonylamino, n-butylcarbonylamino and tert-butylcarbonylamino.

For example and with preference, alkylsulphonyl is methylsulphonyl, ethylsulphonyl, n-propylsulphonyl, isopropylsulphonyl, n-butylsulphonyl and tert-butylsulphonyl.

Alkylaminosulphonyl is an alkylaminosulphonyl radical having one or two (independently selected) alkyl substituents, for example and with preference methylaminosulphonyl, ethylaminosulphonyl, n-propylaminosulphonyl, isopropylaminosulphonyl, tert-butylaminosulphonyl, N,N-dimethylaminosulphonyl, N,N-diethylaminosulphonyl, N-ethyl-N-methylaminosulphonyl, N-methyl-N-n-propylaminosulphonyl, N-isopropyl-N-n-propylaminosulphonyl and N-tert-butyl-N-methylaminosulphonyl. $C_1$-$C_4$-Alkylaminosulphonyl is, for example, a monoalkylaminosulphonyl radical having 1 to 4 carbon atoms or a dialkylaminosulphonyl radical having in each case 1 to 4 carbon atoms per alkyl substituent.

For example and with preference, alkylsulphonylamino is methylsulphonylamino, ethylsulphonylamino, n-propylsulphonylamino, isopropylsulphonylamino, n-butylsulphonylamino and tert-butylsulphonylamino.

Cycloalkyl is a monocyclic cycloalkyl group having generally 3 to 6 carbon atoms; preferred examples of cycloalkyl include cyclopropyl, cyclobutyl, cyclopentyl and cyclohexyl.

Heterocyclyl is a monocyclic heterocyclic radical having 5 or 6 ring atoms and up to 3, preferably up to 2, heteroatoms and/or hetero groups from the group of N, O, S, SO, $SO_2$, where a nitrogen atom may also form an N-oxide. The heterocyclyl radicals can be saturated or partially unsaturated. Preference is given to 5- or 6-membered monocyclic saturated heterocyclyl radicals having up to two heteroatoms from the group consisting of O, N and S, for example and with preference pyrrolidin-2-yl, pyrrolidin-3-yl, pyrrolinyl, tetrahydrofuranyl, tetrahydrothienyl, pyranyl, piperidin-1-yl, piperidin-2-yl, piperidin-3-yl, piperidin-4-yl, thiopyranyl, morpholin-1-yl, morpholin-2-yl, morpholin-3-yl, piperazin-1-yl, piperazin-2-yl.

Halogen is fluorine, chlorine, bromine and iodine, preferably fluorine and chlorine.

In the formulae of the group which may be $R^1$, the end point of the line marked by * does not represent a carbon atom or a $CH_2$ group, but is part of the bond to the atom to which $R^1$ is attached.

In the formulae of the group which may be $R^6$, the end point of the line marked by # does not represent a carbon atom or a $CH_2$ group, but is part of the bond to the atom to which $R^6$ is attached.

Preference is given to compounds of the formula (I) in which $R^1$ is a group of the formula

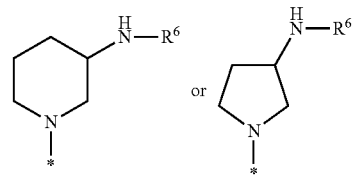

where
* is the attachment site to the heterocycle,
$R^6$ is pyrid-2-yl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,2-pyrazol-5-yl,
where pyrid-2-yl, pyrimid-2-yl, 1,3-thiazol-2-yl and 1,3-thiazol-4-yl are substituted by 1 to 2 substituents, where the substituents are each independently selected from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl,
in which alkyl, alkylamino, alkylcarbonyl, alkylaminocarbonyl and cycloalkylcarbonyl may be substituted by one substituent, where the substituent is selected from the group consisting of halogen, cyano, hydroxyl, amino, trifluoromethyl and $C_3$-$C_6$-cycloalkyl,
and
where 2-aminopyrimid-4-yl, 2-cyclopropylaminopyrimid-4-yl, 2-methylaminopyrimid-4-yl, 2-ethylaminopyrimid-4-yl and 1,2-pyrazol-5-yl may each be substituted by 1 to 2 substituents, where the substituents are each independently selected from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl,
$R^2$ is phenyl,
where phenyl may be substituted by 1 to 3 substituents, where the substituents are each independently selected from the group consisting of chlorine, fluorine, trifluoromethyl, trifluoromethoxy, methyl and methoxy,
$R^3$ is hydrogen,
either
$R^4$ is hydrogen, and
R$^5$ is halogen, cyano, trifluoromethyl, hydroxycarbonyl, aminocarbonyl, C$_1$-C$_4$-alkyl, C$_1$-C$_4$-alkoxycarbonyl, C$_1$-C$_4$-alkylaminocarbonyl or 5- or 6-membered heterocyclylcarbonyl,
  where heterocyclylcarbonyl may be substituted by 1 to 3 substituents, where the substituents are each independently selected from the group consisting of oxo, halogen, C$_1$-C$_4$-alkyl, C$_1$-C$_4$-alkoxy, C$_1$-C$_4$-alkylamino, C$_1$-C$_4$-alkylcarbonyl, C$_1$-C$_4$-alkoxycarbonyl and C$_1$-C$_4$-alkylaminocarbonyl,
  and
  where alkylaminocarbonyl may be substituted by one substituent, where the substituent is selected from the group consisting of hydroxyl, amino, hydroxycarbonyl, aminocarbonyl, C$_1$-C$_4$-alkoxy, C$_1$-C$_4$-alkylamino and 5- or 6-membered heterocyclyl,
    in which heterocyclyl may be substituted by 1 to 2 substituents, where the substituents are each independently selected from the group consisting of oxo, halogen, C$_1$-C$_4$-alkyl, C$_1$-C$_4$-alkoxy, C$_1$-C$_4$-alkylamino, C$_1$-C$_4$-alkylcarbonyl, C$_1$-C$_4$-alkoxycarbonyl and C$_1$-C$_4$-alkylaminocarbonyl,
or
R$^4$ is trifluoromethyl,
and
R$^5$ is cyano,
and the salts thereof, solvates thereof and the solvates of the salts thereof.

Preference is also given to compounds of the formula (I) in which
R$^1$ is a group of the formula

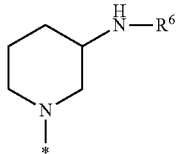

where
* is the attachment site to the heterocycle,
R$^6$ is pyrid-2-yl or 1,3-thiazol-2-yl,
  where pyrid-2-yl and 1,3-thiazol-2-yl are substituted by 1 to 2 substituents, where the substituents are each independently selected from the group consisting of cyano, nitro, amino, trifluoromethylcarbonyl, ethylcarbonyl and methylcarbonyl,
R$^2$ is phenyl,
  where phenyl is substituted by 1 or 2 substituents, where the substituents are each independently selected from the group consisting of chlorine, fluorine, trifluoromethyl, trifluoromethoxy, methyl and methoxy,
R$^3$ is hydrogen,
either
R$^4$ is hydrogen,
and
R$^5$ is cyano, trifluoromethyl, hydroxycarbonyl, methoxycarbonyl, ethoxycarbonyl, C$_1$-C$_2$-alkylaminocarbonyl, piperazinylcarbonyl, piperidinylcarbonyl or morpholinylcarbonyl,
  where piperazinylcarbonyl, piperidinylcarbonyl and morpholinylcarbonyl may each be substituted by 1 to 3 substituents, where the substituents are each independently selected from the group consisting of oxo, halogen and C$_1$-C$_4$-alkyl,
  and
  where alkylaminocarbonyl may be substituted by one substituent, where the substituent is selected from the group consisting of piperazinyl, piperidinyl and morpholinyl,
    where piperazinyl, piperidinyl and morpholinyl may each be substituted by 1 to 2 substituents, where the substituents are each independently selected from the group consisting of oxo, halogen and C$_1$-C$_4$-alkyl,
or
R$^4$ is trifluoromethyl,
and
R$^5$ is cyano,
and the salts thereof, solvates thereof and the solvates of the salts thereof.

Particular preference is given to compounds of the formula (I) in which
R$^1$ is a group of the formula

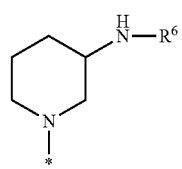

where
* is the attachment site to the heterocycle,
R$^6$ is a group of the formula

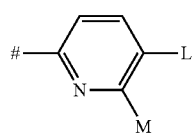

where
# is the attachment site to NH,
L is cyano, nitro or trifluoromethylcarbonyl,
M is hydrogen or amino,
R$^2$ is phenyl,
  where phenyl is substituted by 1 or 2 substituents, where the substituents are each independently selected from the group consisting of chlorine, fluorine and methoxy,
R$^3$ is hydrogen,
either
R$^4$ is hydrogen,
and
R$^5$ is cyano, hydroxycarbonyl, methoxycarbonyl, methylaminocarbonyl, dimethylaminocarbonyl, piperazinylcarbonyl or piperidinylcarbonyl,
  where piperazinylcarbonyl and piperidinylcarbonyl are each substituted by 1 to 2 substituents, where the substituents are each independently selected from the group consisting of halogen and C$_1$-C$_4$-alkyl,
  and
  where methylaminocarbonyl and dimethylaminocarbonyl are substituted by one piperidinyl substituent,
    in which piperidinyl is substituted by 1 to 2 substituents, where the substituents are each independently selected from the group consisting of halogen and C$_1$-C$_4$-alkyl,
or
R$^4$ is trifluoromethyl,
and
R$^5$ is cyano,
and the salts thereof, solvates thereof and the solvates of the salts thereof.

Particular preference is given to compounds of the formula (I) in which
R¹ is a group of the formula

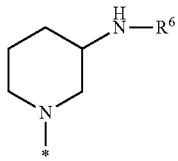

where
* is the attachment site to the heterocycle,
R⁶ is a group of the formula

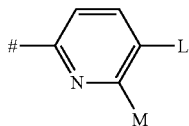

where
# is the attachment site to NH,
either
L is cyano,
and
M is hydrogen,
or
L is cyano, nitro or trifluoromethylcarbonyl,
and
M is amino,
R² is phenyl,
where phenyl is substituted by 1 or 2 substituents, where the substituents are each independently selected from the group consisting of chlorine, fluorine and methoxy,
R³ is hydrogen,
either
R⁴ is hydrogen,
and
R⁵ is cyano, hydroxycarbonyl, methoxycarbonyl, methylaminocarbonyl, dimethylaminocarbonyl, piperazinylcarbonyl or piperidinylcarbonyl,
where piperazinylcarbonyl and piperidinylcarbonyl are each substituted by 1 to 2 substituents, where the substituents are each independently selected from the group consisting of halogen and $C_1$-$C_4$-alkyl,
and
where methylaminocarbonyl and dimethylaminocarbonyl are substituted by one piperidinyl substituent,
in which piperidinyl is substituted by 1 to 2 substituents, where the substituents are each independently selected from the group consisting of halogen and $C_1$-$C_4$-alkyl,
or
R⁴ is trifluoromethyl,
and
R⁵ is cyano,
and the salts thereof, solvates thereof and the solvates of the salts thereof.
Preference is also given to compounds of the formula (I) in which R¹ is a group of the formula

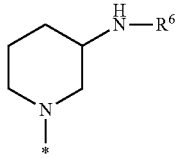

where * is the attachment site to the heterocycle.

Preference is also given to compounds of the formula (I) in which
R⁶ is pyrid-2-yl or 1,3-thiazol-2-yl,
where pyrid-2-yl and 1,3-thiazol-2-yl are substituted by 1 to 2 substituents, where the substituents are each independently selected from the group consisting of cyano, nitro, amino, trifluoromethylcarbonyl, ethylcarbonyl and methylcarbonyl.

Preference is also given to compounds of the formula (I) in which
R⁶ is a group of the formula

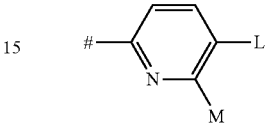

where
# is the attachment site to NH,
L is cyano, nitro or trifluoromethyl,
M is hydrogen or amino.

Preference is also given to compounds of the formula (I) in which R⁶ is 5-cyanopyrid-2-yl.

Preference is also given to compounds of the formula (I) in which R⁶ is 5-trifluoromethylcarbonyl-6-aminopyrid-2-yl.

Preference is also given to compounds of the formula (I) in which
R² is phenyl,
where phenyl is substituted by 1 or 2 substituents, where the substituents are each independently selected from the group consisting of chlorine, fluorine and methoxy.

Preference is also given to compounds of the formula (I) in which R³ is hydrogen.

Preference is also given to compounds of the formula (I) in which
either
R⁴ is hydrogen,
and
R⁵ is cyano, hydroxycarbonyl, methoxycarbonyl, methylaminocarbonyl, dimethylaminocarbonyl, piperazinylcarbonyl or piperidinylcarbonyl,
where piperazinylcarbonyl and piperidinylcarbonyl are each substituted by 1 to 2 substituents, where the substituents are each independently selected from the group consisting of halogen and $C_1$-$C_4$-alkyl,
and
where methylaminocarbonyl and dimethylaminocarbonyl are substituted by one piperidinyl substituent,
in which piperidinyl is substituted by 1 to 2 substituents, where the substituents are each independently selected from the group consisting of halogen and $C_1$-$C_4$-alkyl,
or
R⁴ is trifluoromethyl,
and
R⁵ is cyano.

The invention further provides a process for preparing the compounds of the formula (I), or the salts thereof, solvates thereof and the solvates of the salts thereof, wherein either

[A] the compounds of the formula

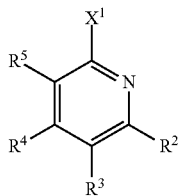

(II)

in which
R², R³, R⁴ and R⁵ are each as defined above,
and
X¹ is halogen, preferably chlorine or fluorine,
are reacted with compounds of the formula

(III)

in which
R¹ is as defined above,
or
[B] the compounds of the formula

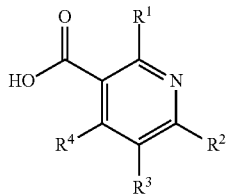

(Ia)

in which
R¹, R², R³ and R⁴ are each as defined above
are reacted with compounds of the formula

(IV)

in which
$R^{5a}$ is $C_1$-$C_4$-alkoxy, $C_1$-$C_4$-alkylamino or 5- to 6-membered heterocyclyl,
  where heterocyclyl may be substituted by 1 to 3 substituents, where the substituents are each independently selected from the group consisting of oxo, halogen, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
and
  where alkylamino may be substituted by one substituent, where the substituent is selected from the group consisting of hydroxyl, amino, hydroxycarbonyl, aminocarbonyl, $C_1$-$C_4$-alkoxy, $C_1$-$C_4$-alkylamino and 5- or 6-membered heterocyclyl,
    in which heterocyclyl may be substituted by 1 to 2 substituents, where the substituents are each independently selected from the group consisting of oxo, halogen, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
to give compounds of the formula

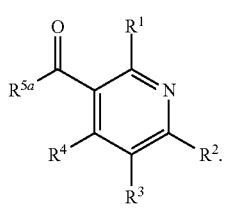

(Ib)

The compounds of the formulae (Ia) and (Ib) are a subset of the compounds of the formula (I).

The reaction according to process [A] is generally effected in inert solvents, optionally in the presence of a base, optionally in a microwave, preferably in a temperature range from 50° C. to 200° C. at standard pressure to 5 bar.

Bases are, for example, alkali metal carbonates, for example sodium carbonate, potassium carbonate or caesium carbonate, or organic bases such as trialkylamines, e.g. triethylamine, N-methylmorpholine, N-methylpiperidine, 4-dimethylaminopyridine or diisopropylethylamine, or other bases, for example sodium hydride or potassium tert-butoxide; preference is given to diisopropylethylamine or sodium hydride.

Inert solvents are, for example, halohydrocarbons such as methylene chloride or trichloromethane, alcohols such as methanol, ethanol, n-propanol or isopropanol, or ethers such as dioxane or tetrahydrofuran, or other solvents, for example dimethyl sulphoxide, dimethylformamide or N-methylpyrrolidone, or mixtures of these solvents, preference being given to N-methylpyrrolidone or dimethyl sulphoxide.

The compounds of the formula (II) are known, can be synthesized from the corresponding starting compounds by known processes or can be prepared analogously to the processes described in the Examples section (Examples 16A and 17A) or analogously to W. Yang et al., Organic Letters 2003, 5, 17, 3131.

The compounds of the formula (III) are known, can be synthesized from the corresponding starting compounds by known processes or can be prepared analogously to the processes described in the Examples section (Examples 1A to 15A).

The reaction according to process [B] is generally effected in inert solvents, in the presence of a dehydrating reagent, optionally in the presence of a base, preferably within a temperature range from room temperature up to reflux of the solvents at standard pressure.

Inert solvents are, for example, halohydrocarbons such as methylene chloride, trichloromethane or 1,2-dichloroethane, ethers such as dioxane, tetrahydrofuran or 1,2-dimethoxyethane, or other solvents such as acetone, dimethylformamide, dimethylacetamide, 2-butanone or acetonitrile. It is equally possible to use mixtures of the solvents. Preference is given to dimethylformamide.

Suitable dehydrating reagents in this context are, for example, carbodiimides, for example N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide), or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures thereof, with bases.

Bases are, for example, alkali metal carbonates, for example sodium carbonate or potassium carbonate, or sodium hydrogencarbonate or potassium hydrogencarbonate, or organic bases such as trialkylamines, e.g. triethylamine, N-methylmorpholine, N-methylpiperidine, 4-dimethylaminopyridine or diisopropylethylamine; preference is given to diisopropylethylamine.

Preference is given to performing the condensation with HATU in the presence of diisopropylethylamine.

The compounds of the formula (Ia) can be prepared according to process [A]. During the reaction, the carboxylic acid is protected in the form of the methyl or ethyl ester, which is hydrolysed in the last stage with a base, for example sodium hydroxide, potassium hydroxide or lithium hydroxide, to prepare the compounds of the formula (Ia).

The preparation of the starting compounds and of the compounds of the formula (I) can be illustrated by the synthesis schemes which follow.

Scheme 1:

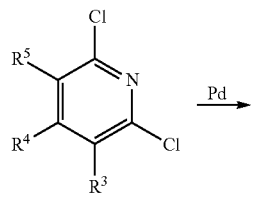

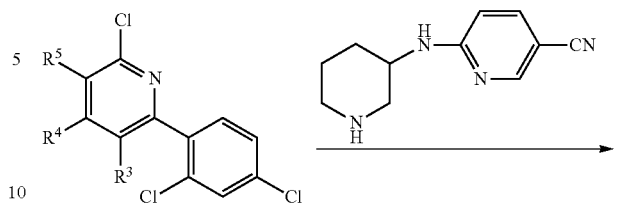

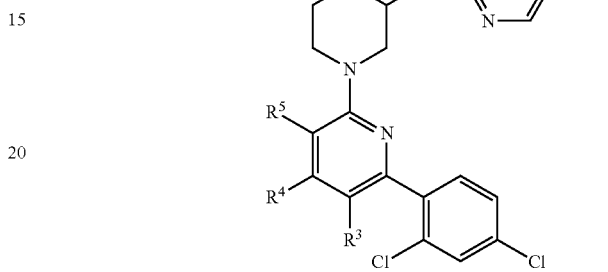

Scheme 2:

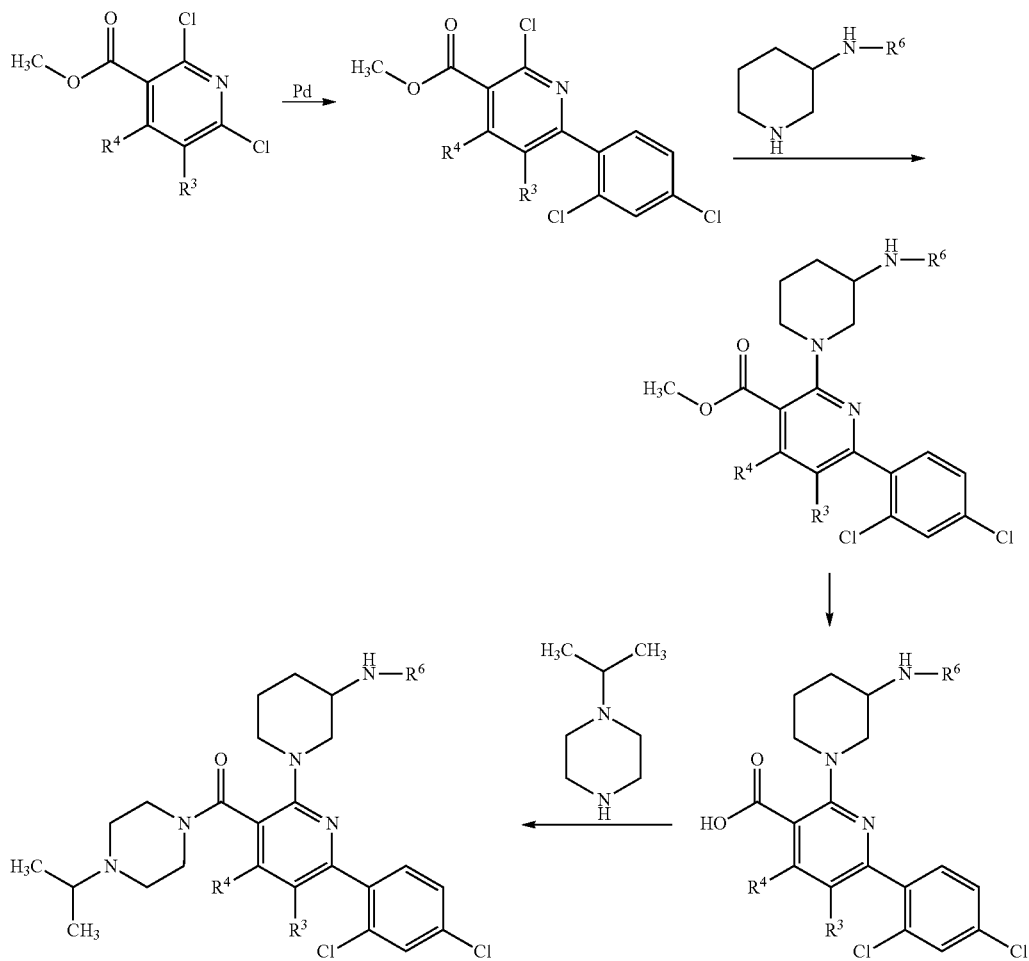

The inventive compounds have an unforeseeable useful spectrum of pharmacological and pharmacokinetic activity.

They are therefore suitable for use as medicaments for treatment and/or prophylaxis of diseases in humans and animals.

The present invention further provides for the use of the inventive compounds for treatment and/or prophylaxis of disorders, preferably haematological disorders, especially leukopenia and neutropenia.

The inventive compounds are therefore suitable for prophylaxis and/or treatment of neurodegenerative disorders, for example Alzheimer's, Parkinson's, schizophrenia, degeneration, dementia, depression; aggression, cerebrovascular ischaemia, sleep disorders, Huntington's chorea, neurotraumatic disorders, for example stroke; type 2 diabetes mellitus and associated disorders, for example metabolic syndrome or obesity, type 1 diabetes mellitus, diabetic nephropathy, diabetic neuropathy, diabetic retinopathy, glomerulonephritis, hypercalcaemia, hyperglycaemia, hyperlipidaemia, glucose-galactose malabsorption, general endocrine dysfunctions, for example pancreatitis; haematological disorders, for example acquired and congenital neutropenia, medicament-induced neutropenia, parasite-induced neutropenia, chemotherapy-induced neutropenia, granulocytopenia, acquired and congenital leucopenia, acquired and congenital anaemia, haemolytic anaemia, sickle cell anaemia, acquired and congenital thrombocytopenia, leukocyte dysfunctions, blood coagulation disorders, graft-versus-host reaction; cancer, for example breast carcinoma, colon tumour, gastrointestinal tumours, Hodgkin's lymphoma, non-Hodgkin's lymphoma, Kaposi's sarcoma, hepatic tumour, pancreatic tumour, skin tumour, bone marrow tumour, leukaemias, for example acute lymphatic leukaemia, acute myeloid leukaemia, chronic myeloid leukaemia, chronic lymphatic leukaemia, MLL leukaemia, prostate tumours, lung cancer, renal tumours; asthma, progressive, incompletely reversible obstruction of the respiratory tract, pneumonia, pulmonary dysfunction; inflammatory disorders, for example autoimmune diseases such as multiple sclerosis, rheumatoid arthritis; infections by gram-negative and gram-positive bacteria, viral infections, fungal infections, for example by *Candida albicans*, HIV infections and HIV-associated infections, hepatitis type A, B and C, parasitic infections; malaria; hair loss; reduced sperm motility; wound healing; glaucoma; osteoporosis, bone marrow disorders, bone and joint disorders; cardiovascular disorders, for example cardiac defects, heart failure, cardiac fibrosis, cardiac arrhythmias, myocardial infarction, medicament- or substance-induced cardiotoxicity, atherosclerosis, high blood pressure; sepsis; inflammatory disorders; pemphigus vulgaris.

The inventive compounds are particularly suitable for prophylaxis and/or treatment of neurodegenerative disorders, for example Alzheimer's and schizophrenia, of type 2 diabetes mellitus and associated disorders, of cancer, of leukopenia and/or of neutropenia.

The inventive compounds are particularly suitable for prophylaxis and/or treatment of leukopenia and/or of neutropenia.

The inventive compounds can additionally also be used for efficient ex vivo propagation of adult haematopoietic stem cells from bone marrow and/or from peripheral blood and/or for ex vivo propagation of embryonic stem cells from umbilical cord blood.

The inventive compounds can additionally also be used for ex vivo propagation of embryonic and/or adult stem cells and for ex vivo differentiation of embryonic and/or adult stem cells.

These cells expanded in this way can then be used to curtail the cytopenias induced by myeloablative therapies or within the framework of therapeutic transplantation methods or for haematological systemic disorders, for example leukaemias, or with cells which have been genetically manipulated after expansion for gene therapies.

The present invention further provides for the use of the inventive compounds for treatment and/or prophylaxis of disorders, especially the disorders mentioned above.

The present invention further provides for the use of the inventive compounds for producing a medicament for treatment and/or prophylaxis of disorders, especially the disorders mentioned above.

The present invention further provides a method for treatment and/or prophylaxis of disorders, especially the disorders mentioned above, using a therapeutically effective amount of an inventive compound.

The present invention further provides medicaments comprising an inventive compound and one or more further active ingredients, especially for treatment and/or prophylaxis of the disorders mentioned above. Preferred examples of suitable active ingredient combinations include:

A combination of the inventive compounds with chemotherapeutic agents used clinically may lead to a significantly improved treatment outcome for various neoplastic diseases. The chemotherapeutic agents are substances which either inhibit the rate of division of tumour cells and/or prevent neovascularization of solid tumours. These include substances from the group of taxanes, for example paclitaxel or docetaxel, substances which inhibit the mitosis of tumour cells, for example vinblastine, vincristine, vindesine or vinorelbine. Substances from the class of platinum derivatives, for example cisplatin, carboplatin, oxaliplatin, nedaplatin or lobaplatin. The chemotherapeutic agents further include substances from the class of alkylating agents, for example cyclophosphamide, ifosfamide, melphalan, chlorambucil, pipobroman, triethylene melamine, busulphan, carmustine, lomustine, streptozin, dacarbazine or temozolomide. The chemotherapeutic agents also include antimetabolites, for example, folic acid antagonists, pyrimidine analogues, purine analogues or adenosine deaminase inhibitors. This class of substances includes inter alia methotrexate, 5-fluorouracil, floxuridine, cytarabine, pentostatin and gemcitabine. Also used as chemotherapeutic agents are natural products or derivatives thereof, which include enzymes, antitumour antibodies and lymphokines. These include for example bleomycin, dactinomycin, daunorubicin, doxorubicin, epirubicin, idarubicin, ara-V, paclitaxel, mithramycin, mitomycin-C, L-asparaginase, interferons (e.g. IFN-alpha) and etoposide. Other chemotherapeutic agents with antiproliferative and/or anti-angiogenetic effect are sorafenib, sunitinib, bortezomib, DAST inhibitor (BAY 73-4506), ZK-epothilone inter alia.

The present invention further provides a method for ex vivo propagation of adult haematopoietic stem cells from bone marrow and/or from peripheral blood and/or for ex vivo propagation of embryonic stem cells from umbilical cord blood, which is characterized in that an effective amount of the inventive compound is added.

The inventive compounds may act systemically and/or locally. For this purpose, they can be administered in a suitable manner, for example by the oral, parenteral, pulmonary, nasal, sublingual, lingual, buccal, rectal, dermal, transdermal, conjunctival or otic route, or as implant or stent.

The inventive compounds can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay and control the release of the inventive compound), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

Oral administration is preferred.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The inventive compounds can be converted to the administration forms mentioned. This can be done in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and masking flavours and/or odours.

The present invention further provides medicaments comprising at least one inventive compound, preferably together with one or more inert nontoxic pharmaceutically suitable excipients, and the use thereof for the purposes mentioned above.

In the case of parenteral administration, it has generally been found to be advantageous to administer amounts of about 5 to 1500 mg every 24 hours to achieve effective results. In the case of oral administration, the amount is about 5 to 2000 mg every 24 hours.

It may nevertheless be necessary in some cases to deviate from the stated amounts, specifically as a function of the body weight, route of administration, individual response to the active ingredient, nature of the preparation and time or interval over which administration takes place.

The percentages in the tests and examples which follow are, unless stated otherwise, percentages by weight; parts are parts by weight. Solvent ratios, dilution ratios and concentration data for liquid/liquid solutions are based in each case on volume. "w/v" means "weight/volume". For example, "10% w/v" means: 100 ml of solution or suspension comprise 10 g of substance.

A) Examples

Abbreviations abs. absolute
Boc tert-butoxycarbonyl
$CDCl_3$ deuterochloroform
d day
DIEA N,N-diisopropylethylamine
DMAP 4-N,N-dimethylaminopyridine
DMF dimethylformamide
DMSO dimethyl sulphoxide
EDC N'-(3-dimethylaminopropyl)-N-ethylcarbodiimide× HCl
eq. equivalent
ESI electrospray ionization (in MS)
sat. saturated
h hour
HOBt 1-hydroxy-1H-benzotriazole×$H_2O$
HPLC high-pressure high-performance liquid chromatography
conc. concentrated
LC-MS liquid chromatography-coupled mass spectrometry
min minutes
MS mass spectrometry
MW molecular weight [g/mol]
NMR nuclear magnetic resonance spectroscopy
OAc acetate
OEt ethoxy
p.a. for analysis
PyBOP 1-benzotriazolyloxytripyrrolidinophosphonium hexafluorophosphate
$R_f$ retention index (in TLC)
RP-HPLC reversed phase HPLC
RT room temperature
$R_t$ retention time (in HPLC)
TBTU (benzotriazol-1-yloxy)bisdimethylaminomethylium fluoroborate
TFA trifluoroacetic acid
THF tetrahydrofuran
LC-MS Methods:

Method 1: Instrument: Micromass Quattro LCZ with HPLC Agilent series 1100; column: Phenomenex Synergi 2.5μ MAX-RP 100A Mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 2: MS instrument type: Micromass ZQ; HPLC instrument type: Waters Alliance 2795; column: Merck Chromolith SpeedROD RP-18e 100 mm×4.6 mm; eluent A: water+500 μl of 50% formic acid/1; eluent B: acetonitrile+500 μl of 50% formic acid/1; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm Method 3: MS instrument type: Micromass ZQ; HPLC instrument type: HP 1100 Series; UV DAD; column: Phenomenex Gemini 3μ, 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4: Instrument: Micromass Platform LCZ with HPLC Agilent Series 1100; column: Thermo Hypersil GOLD 3μ, 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 5: MS instrument type: Waters ZQ; HPLC instrument type: Waters Alliance 2795; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 210 nm.

Method 6: MS instrument type: Micromass ZQ; HPLC instrument type: Waters Alliance 2795; column: Phenomenex Synergi 2.5µ MAX-RP 100A Mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 7: Instrument: Micromass Quattro LCZ with HPLC Agilent series 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.

Method 8: Instrument: Micromass QuattroPremier with Waters HPLC Acquity; column: Thermo Hypersil GOLD 1.9µ, 50 mm×1 mm; eluent A: 1 l of water+0.5 ml of 50% formic acid, eluent B: 1 l of acetonitrile+0.5 ml of 50% formic acid; gradient: 0.0 min 100% A→0.1 min 100% A→1.5 min 10% A→2.2 min 10% A; oven: 50° C.; flow rate: 0.33 ml/min; UV detection: 210 nm.

Method 9: Instrument: Micromass Quattro Micro MS with HPLC Agilent series 1100; column: Thermo Hypersil GOLD 3µ, 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10% A→4.01 min 100% A→5.00 min 100% A; flow rate: 0.0 min/3.0 min/4.0 min/4.01 min 2.5 ml/min, 5.00 min 2 ml/min; oven: 50° C.; UV detection: 210 nm.

Method 10: Preparative HPLC: column: Reprosil C18; gradient: acetonitrile/water with 0.1% hydrochloric acid.

Method 11: Preparative HPLC: column: Reprosil C18; gradient: acetonitrile/water with 0.1% trifluoroacetic acid.

Method 12: Instrument: Waters ACQUITY SQD HPLC System; column: Waters Acquity HPLC HSS T3 1.8µ, 50 mm×1 mm; eluent A: 1 l of water+0.25 ml of 99% formic acid, eluent B: 1 l of acetonitrile+0.25 ml of 99% formic acid; gradient: 0.0 min 90% A→1.2 min 5% A→2.0 min 5% A; flow rate: 0.40 ml/min; oven: 50° C.; UV detection: 210-400 nm.

Method 13: Preparative HPLC: column: Reprosil C18; gradient: acetonitrile/water.

The microwave reactor used was a single-mode instrument of the Emrys™ Optimizer type.

Starting Compounds

Example 1A tert-Butyl (6-chloropyridin-2-yl)carbamate

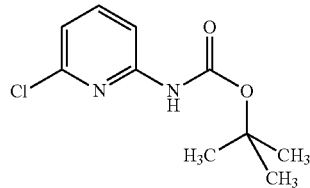

23.4 g (181.8 mmol) of 2-chloro-5-aminopyridine were admixed with 150 ml of THF under argon and cooled to 0° C. 73.3 g (400 mmol) of sodium bis(trimethylsilyl)amide and 43.65 g (200 mmol) of di-tert-butyl dicarbonate, dissolved in 150 ml of THF, were added dropwise. After 15 min, the cooling bath was removed and the mixture was stirred at RT for a further 15 min. The THF was removed by rotary evaporation, and the residue was admixed and extracted with ethyl acetate and 0.5 N hydrochloric acid. The organic phase was removed, dried over magnesium sulphate and concentrated on a rotary evaporator. The reaction mixture was chromatographed on silica gel (eluent: dichloromethane/methanol 100%→100:3). 36.54 g (88% of theory) of the product were obtained in solid form.

LCMS (method 3): $R_t$=2.41 min (m/z=175 (M+H)$^+$).

$^1$H NMR (400 MHz, DMSO-d$_6$): δ=10.11 (s, 1H), 7.78 (d, 2H), 7.1 (t, 1H), 1.47 (s, 9H).

Example 2A tert-Butyl (6-chloro-3-formylpyridin-2-yl)carbamate

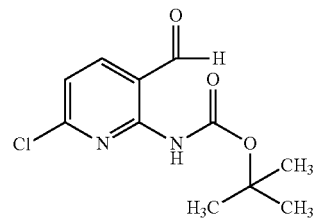 [SMILES: CC(C)(C)OC(=O)Nc1nc(Cl)ccc1C=O]

The reaction apparatus was baked out, and the reaction was effected under argon and was stirred. 15 g (65.6 mmol) of tert-butyl (6-chloropyridin-2-yl)carbamate (Example 1A) and 19 g (164 mmol) of 1,2-bis(dimethylamino)ethane were initially charged in 270 ml of THF and cooled to –78° C. 102.5 ml (164 mmol) of butyllithium (1.6 N) were added dropwise. After the dropwise addition had ended, the reaction was warmed gradually to –10° C. and kept at –10° C. for 2 h. Then it was cooled again to –78° C., and 10 ml (131 mmol) of DMF were added. The reaction was warmed gradually to RT and the reaction mixture was added to 1 l of ethyl acetate and 350 ml of 1 N hydrochloric acid, the mixture was stirred for 15 min and the organic phase was removed. It was washed with water and saturated sodium hydrogencarbonate solution, dried over magnesium sulphate and concentrated on a rotary evaporator. The residue was admixed with diethyl ether, and the solids were filtered off with suction and dried. 12.3 g (73% of theory) of the product were obtained in solid form.

LCMS (method 3): $R_t$=2.19 min (m/z=255 (M+H)$^-$).

$^1$H NMR (400 MHz, DMSO-d$_6$): δ=10.37 (s, 1H), 9.83 (s, 1H), 8.2 (d, 1H), 7.42 (d, 1H), 1.46 (s, 9H).

Example 3A tert-Butyl {6-chloro-3-[(hydroxyimino)methyl]pyridin-2-yl}carbamate

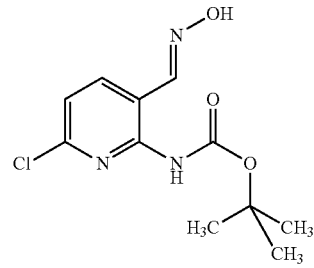 [SMILES: CC(C)(C)OC(=O)Nc1nc(Cl)ccc1/C=N/O]

15.45 g (60.2 mmol) of tert-butyl (6-chloro-3-formylpyridin-2-yl)carbamate (Example 2A) were initially charged in 750 ml of ethanol and admixed with a solution of 225 ml of water and 9.38 g (120.4 mmol) of sodium acetate and stirred for 5 min. A solution of 225 ml of water and 8.36 g (114.4 mmol) of hydroxylamine hydrochloride was added and the mixture was stirred at RT for 4 h. At 20° C., the reaction mixture was concentrated on a rotary evaporator. The residue was taken up in ethyl acetate and washed twice with saturated sodium hydrogencarbonate solution and once with saturated sodium chloride solution. The organic phase was removed, dried over magnesium sulphate and concentrated at 20° C. on a rotary evaporator. 15.5 g (80% of theory) of the product were obtained in solid form.

LCMS (method 3): $R_t$=2.08 min (m/z=270 (M+H)$^-$).

$^1$H NMR (400 MHz, DMSO-$d_6$): δ=11.71 (s, 1H), 9.91 (s, 1H), 8.14 (s, 1H), 8.02 (d, 1H), 7.3 (d, 1H), 1.49 (s, 9H).

Example 4A

2-Amino-6-chloropyridine-3-carbaldehyde oxime hydrochloride

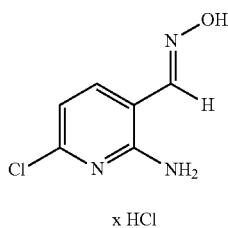 [SMILES: Nc1nc(Cl)ccc1/C=N/O]

x HCl 15.5 g (57 mmol) of tert-butyl {6-chloro-3-[(hydroxyimino)methyl]pyridin-2-yl}carbamate (Example 3A) were dissolved in 285 ml of 4 N hydrogen chloride in dioxane and stirred for a further 30 min. The reaction mixture was concentrated by half and the same amount of diethyl ether was added. The reaction mixture was stirred for a further 20 min and the product was filtered off and washed with diethyl ether. 11 g (94% of theory) of the product were obtained in solid form.

LCMS (method 6): $R_t$=1.09 min (m/z=172 (M+H)$^+$)

$^1$H NMR (400 MHz, DMSO-$d_6$): δ=8.27 (s, 1H), 7.61 (d, 1H), 6.65 (d, 1H).

Example 5A

2-Amino-6-chloropyridine-3-carbonitrile

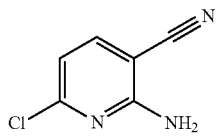

11.15 g (53.6 mmol) of 2-amino-6-chloropyridine-3-carbaldehyde oxime hydrochloride (Example 4A) were initially charged in dioxane, admixed with 13 ml (161 mmol) of pyridine and cooled to 0° C. 8.3 ml (58.95 mmol) of trifluoroacetic anhydride were added, and the reaction was warmed to RT and then stirred at 60° C. for 2 h. The reaction mixture was taken up in a mixture of ethyl acetate and sodium hydrogencarbonate solution. The organic phase was washed with saturated aqueous sodium chloride solution, dried over magnesium sulphate and concentrated on a rotary evaporator. The residue was suspended in 3:1 dichloromethane:diethyl ether, and the solids were filtered off with suction and dried. 5.56 g (66% of theory) of the product were obtained in solid form.

LCMS (method 6): $R_t$=1.0 min (m/z=154 (M+H)$^+$).

$^1$H NMR (400 MHz, DMSO-$d_6$): δ=7.91 (d, 1H), 7.38 (s, 2H), 6.69 (d, 1H).

Example 6A 4-(Trifluoroacetyl)morpholine

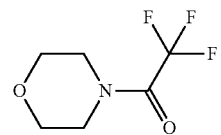 [SMILES: O=C(N1CCOCC1)C(F)(F)F]

15 g (172 mmol) of morpholine were initially charged in 750 ml of dichloromethane, and 29 ml (206 mmol) of trifluoroacetic anhydride and 119 ml (688 mmol) of N,N-diisopropylethylamine were added at 0° C. The reaction mixture was warmed to RT and stirred at RT for a further 3 h. The reaction mixture was concentrated and the residue was taken up in ethyl acetate and washed successively with aqueous sodium hydrogencarbonate solution, 1 N hydrochloric acid and again with aqueous sodium hydrogencarbonate solution. The organic phase was dried over magnesium sulphate and concentrated on a rotary evaporator. 28 g (88% of theory) of the product were obtained as an oil.

LCMS (method 9): $R_t$=1.22 min (m/z=184 (M+H)$^+$)

$^1$H NMR (400 MHz, DMSO-$d_6$): δ=3.65 (m, 2H), 3.56 (m, 2H).

Example 7A tert-Butyl (6-chloro-3-(trifluoroacetyl)pyridin-2-yl)carbamate

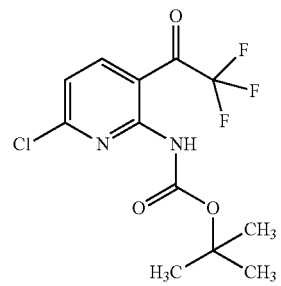 [SMILES: CC(C)(C)OC(=O)Nc1nc(Cl)ccc1C(=O)C(F)(F)F]

8 g (35 mmol) of tert-butyl (6-chloropyridin-2-yl)carbamate (Example 1A) were initially charged in 100 ml of THF and cooled to −50° C. 55 ml (87 mmol) of butyllithium (1.6 N) were added dropwise. After the dropwise addition had ended, the reaction was warmed gradually to −10° C. and stirred at 0° C. for 2 h. Subsequently, the mixture was cooled again to −40° C., and 12.8 g (70 mmol) of 4-(trifluoroacetyl)morpholine (Example 6A), dissolved in 4 ml of THF, were added. The reaction solution was stirred at −40° C. for 1 h, then poured at −40° C. onto 1 l of ethyl acetate and 350 ml of ammonium chloride solution, and extracted. The organic phase was removed, dried over magnesium sulphate and concentrated on a rotary evaporator. The reaction mixture was chromatographed on silica gel (eluent: cyclohexane/ethyl acetate 10:1). 9 g (79% of theory) of the product were obtained as an oil.

$^1$H NMR (400 MHz, DMSO-d$_6$): δ=10.96 (s, 1H), 7.99 (d, 1H), 7.4 (d, 1H), 1.43 (s, 9H).

Example 8A tert-Butyl 3-[(5-cyanopyridin-2-yl)amino]piperidine-1-carboxylate

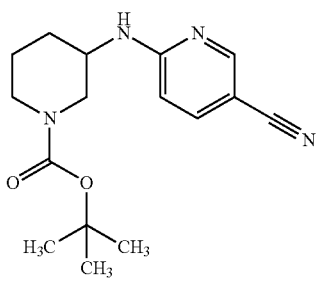 [SMILES: CC(C)(C)OC(=O)N1CCCC(Nc2ccc(C#N)cn2)C1]

1.0 g (4.99 mmol) of tert-butyl 3-aminopiperidine-1-carboxylate and 1.383 g (9.99 mmol) of 6-chloropyridine-3-carbonitrile and 1.29 g (9.99 mmol) of diisopropylethylamine were suspended in 40 ml of DMSO and heated to 140° C. in a microwave reactor for 45 min. The mixture was substantially freed of the DMSO by Kugelrohr distillation and admixed with water, and the precipitating solid was filtered off. After drying under high vacuum, 2.24 g (46% of theory) of the product were obtained.

LCMS (method 3): R$_t$=2.23 min (m/z=303 (M+H)$^+$).

Example 9A tert-Butyl 3-[(6-amino-5-cyanopyridin-2-yl)amino]piperidine-1-carboxylate

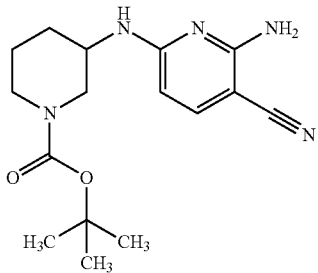 [SMILES: CC(C)(C)OC(=O)N1CCCC(Nc2ccc(C#N)c(N)n2)C1]

2.15 g (10.7 mmol) of tert-butyl 3-aminopiperidine-1-carboxylate, 1.50 g (9.77 mmol) of 2-amino-6-chloropyridine-3-carbonitrile (Example 5A) and 1.89 g (14.7 mmol) of diisopropylethylamine were suspended in 6 ml of DMSO and heated to 130° C. in a microwave reactor for 8 h. The reaction mixture was diluted with ethyl acetate (100 ml) and water (40 ml), and the organic phase was removed and washed with saturated aqueous sodium chloride solution (50 ml), dried over magnesium sulphate and concentrated. The residue was chromatographed on silica gel (eluent: cyclohexane/ethyl acetate 4:1 to 1:1). 2.04 g (60% of theory) of the product were isolated in solid form.

LCMS (method 6): R$_t$=1.69 min (m/z=318 (M+H)$^+$)

Example 10A 6-(Piperidin-3-ylamino)pyridine-3-carbonitrile hydrochloride

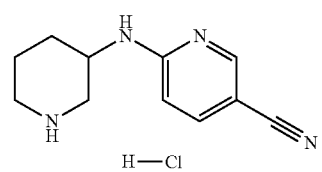

2.24 g (7.4 mmol) of tert-butyl 3-[(5-cyanopyridin-2-yl)amino]piperidine-1-carboxylate (Example 8A) were dissolved in 4.3 ml of a hydrochloric acid solution in dioxane (4 M) and stirred at RT for 3 h. On completion of reaction, the solvent was removed completely. 1.74 g (90% of theory) of the product were obtained in solid form.

LCMS (method 8): R$_t$=0.27 min (m/z=203 (M+H)$^+$)

$^1$H NMR (400 MHz, DMSO-d$_6$): δ=9.13 (m, 1H), 9.0 (m, 1H), 8.44 (d, 1H), 7.89 (m, 1H), 7.74 (dd, 1H), 6.63 (d, 1H), 5.58 (s, br), 4.19 (s, br, 1H), 3.57 (s, 1H), 3.34 (d, 1H), 3.14 (d, 1H), 2.88 (m, 1H), 2.7-2.81 (m, 1H), 1.82-2.0 (m, 2H), 1.63-1.79 (m, 1H), 1.48-1.59 (m, 1H).

Example 11A

2-Amino-6-(piperidin-3-ylamino)pyridine-3-carbonitrile hydrochloride

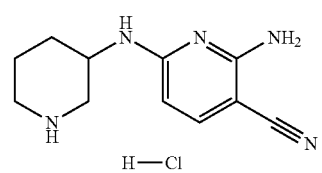

2.00 g (6.3 mmol) of tert-butyl 3-[(6-amino-5-cyanopyridin-2-yl)amino]piperidine-1-carboxylate (Example 9A) were dissolved in 40 ml of a hydrochloric acid solution in dioxane (4 M) and stirred at RT for 2 h. On completion of reaction, the solvent was concentrated by half, and 20 ml of diethyl ether were added. The precipitate was filtered off and dried. 1.80 g (100% of theory) of the product were obtained in solid form.

LCMS (method 8): R$_t$=0.25 min (m/z=218 (M+H)$^+$)

$^1$H NMR (400 MHz, DMSO-d$_6$): δ=9.38 (br m, 1H), 8.97 (br m, 1H), 8.25 (br m, 1H), 7.53 (m, 1H), 7.40 (br s, 2H), 6.01 (d, 1H), 4.16 (br m, 1H), 3.34 (br m, 1H), 3.10 (m, 1H), 2.89 (m, 2H), 2.00-1.84 (m, 2H), 1.73 (m, 1H), 1.55 (m, 1H).

Example 12A tert-Butyl 3-({6-[(tert-butoxycarbonyl)amino]-5-(trifluoroacetyl)pyridin-2-yl}amino)piperidine-1-carboxylate

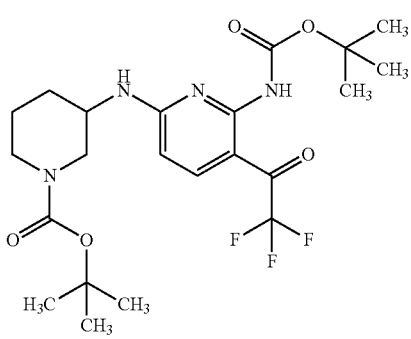 [SMILES: CC(C)(C)OC(=O)Nc1nc(NC2CCCN(C(=O)OC(C)(C)C)C2)ccc1C(=O)C(F)(F)F]

561 mg (2.8 mmol) of tert-butyl 3-aminopiperidine-1-carboxylate, 700 mg (2.16 mmol) of tert-butyl [6-chloro-3-(trifluoroacetyl)pyridin-2-yl]carbamate (Example 7A) and 0.56 ml (3.23 mmol) of diisopropylethylamine were suspended in 14 ml of DMSO and heated to 90° C. in a microwave reactor for 45 min. The reaction mixture was diluted with ethyl acetate (100 ml) and washed with saturated aqueous ammonium chloride solution (3×40 ml) and then with saturated aqueous sodium hydrogencarbonate solution (40 ml). The organic phase was dried over magnesium sulphate and concentrated. The residue was chromatographed on silica gel (eluent: cyclohexane/ethyl acetate 5:1 to 1:1). 670 mg (63% of theory) of the product were isolated.

LCMS (method 6): $R_t$=2.70 min (m/z=489 (M+H)$^+$)

Example 13A

1-[2-Amino-6-(piperidin-3-ylamino)pyridin-3-yl]-2,2,2-trifluoroethanone hydrochloride

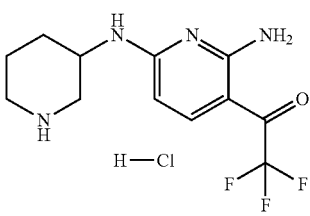

670 mg (1.37 mmol) of tert-butyl 3-({6-[(tert-butoxycarbonyl)amino]-5-(trifluoroacetyl)pyridin-2-yl}amino)piperidine-1-carboxylate (Example 12A) were dissolved in 25 ml of a hydrochloric acid solution in dioxane (4 M) and stirred at RT for 20 h. On completion of reaction, the reaction mixture was diluted with diethyl ether (100 ml), and the precipitate was filtered off completely and washed with diethyl ether (100 ml) and dried. 286 mg (64% of theory) of the product were obtained in solid form.

LCMS (method 6): $R_t$=0.81 min (m/z=289 (M+H)$^+$).

$^1$H NMR (400 MHz, DMSO-d$_6$): δ=9.26 (br s, 1H), 9.07 (br s, 1H), 8.8.34 (br s, 1H), 7.59 (d, 1H), 6.22 (br, 2H), 6.03 (d, 1H), 4.25 (br m, 1H), 3.36 (m, 1H), 3.13 (m, 1H), 2.93 (m, 2H), 2.00-1.85 (m, 2H), 1.73 (m, 1H), 1.56 (m, 1H).

Example 14A tert-Butyl 3-[(6-amino-5-nitropyridin-2-yl)amino]piperidine-1-carboxylate

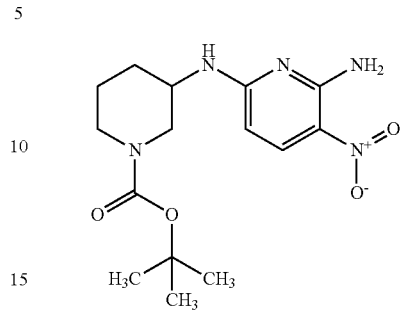

500 mg (2.11 mmol) of tert-butyl 3-aminopiperidine-1-carboxylate, 772 mg (4.22 mmol) of 2-amino-6-chloro-3-nitropyridine and 1.05 ml (6.34 mmol) of diisopropylethylamine were suspended in 18 ml of DMSO and heated to 120° C. in a microwave reactor for 45 min. The reaction mixture was purified by means of preparative reversed-phase HPLC (method 13). 600 mg (81% of theory) of the product were isolated in solid form.

LCMS (method 6): $R_t$=1.77 min (m/z=338 (M+H)$^+$)

Example 15A

3-Nitro-N$^6$-(piperidin-3-yl)pyridine-2,6-diamine hydrochloride

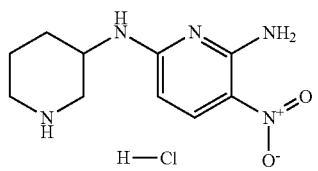

610 mg (1.62 mmol) of tert-butyl 3-[(6-amino-5-nitropyridin-2-yl)-amino]piperidine-1-carboxylate (Example 14A) were dissolved in 40 ml of a hydrochloric acid solution in dioxane (4 M) and stirred at RT for 30 min. On completion of reaction, the solvent was removed completely. 662 mg of the crude product were obtained.

LCMS (method 4): $R_t$=0.86 min (m/z=238 (M+H)$^+$)

Example 16A

Methyl 2-chloro-6-(2,4-dichlorophenyl)pyridine-3-carboxylate

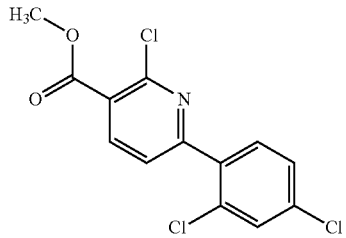 [SMILES: COC(=O)c1ccc(-c2ccc(Cl)cc2Cl)nc1Cl]

6 g (29.12 mmol) of methyl 2,6-dichloropyridine-3-carboxylate, 5.56 g (29.12 mmol) of 2,4-dichlorophenylboronic acid, 12.07 g (87.4 mmol) of potassium carbonate and then 1.68 g (1.46 mmol) of tetrakis(triphenylphosphine)palladium (0) were initially charged in 120 ml of degassed THF, and the mixture was heated under reflux conditions and under an argon atmosphere for 16 h. 300 ml of water and 500 ml of ethyl acetate were added. After separating the phases and removing the solvent, the residue was chromatographed on silica gel (cyclohexane/ethyl acetate 6:1). 2.5 g (27% of theory) of the product were isolated in solid form.

LCMS (method 6): $R_t$=2.41 min (m/z=316 (M+H)$^+$)

$^1$H NMR (400 MHz, DMSO-d$_6$): δ=8.38 (d, 1H), 7.86 (d, 1H), 7.82 (d, 1H), 7.68 (d, 1H), 7.60 (dd, 1H), 3.92 (s, 3H).

Example 17A

Methyl 2-chloro-6-(2-methoxyphenyl)pyridine-3-carboxylate

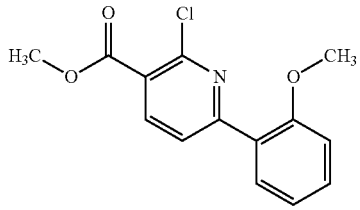

500 mg (1.90 mmol) of 2-chloro-6-(2-methoxyphenyl)pyridine-3-carboxylic acid were initially charged in a mixture of 20 ml of methanol and 8 ml of toluene and admixed with 8 ml (16 mmol) of a 2 molar solution of trimethylsilyldiazomethane in hexane. The mixture was stirred at RT for 15 h and then 1 ml of acetic acid was added. The solvent was removed fully under reduced pressure, and the resulting solid was used without further purification. 502 mg (87% of theory) of the product were obtained.

LCMS (method 8): $R_t$=1.27 min (m/z=278 (M+H)$^+$).

$^1$H NMR (400 MHz, DMSO-d$_6$): δ=8.29 (d, 1H), 8.04 (d, 1H), 7.81 (dd, 1H), 7.50 (dt, 1H), 7.21 (d, 1H), 7.11 (t, 1H), 3.90 (s, 3H), 3.88 (s, 3H).

WORKING EXAMPLES

Example 1

2-{3-[(6-Amino-5-nitropyridin-2-yl)-amino]piperidin-1-yl}-6-(4-chlorophenyl)pyridine-3-carbonitrile

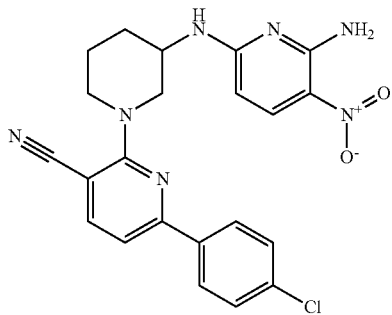 [SMILES: N#Cc1ccc(-c2ccc(Cl)cc2)nc1N1CCCC(Nc2ccc([N+](=O)[O-])c(N)n2)C1]

70.4 mg (0.27 mmol) of 2-chloro-6-(4-chlorophenyl)pyridine-3-carbonitrile, 100 mg (0.32 mmol) of 3-nitro-N$^6$-(piperidin-3-yl)pyridine-2,6-diamine hydrochloride (Example 15A) and 0.187 ml (1.08 mmol) of N,N-diisopropylethylamine were initially charged in 3 ml of DMSO. The mixture was heated at 140° C. in a microwave for 30 min. The crude product was purified by means of preparative HPLC (method 13). 99 mg (74% of theory) of the product were obtained in solid form.

LCMS (method 8): $R_t$=1.45 min (m/z=450 (M+H)$^+$)

$^1$H NMR (400 MHz, DMSO-d$_6$): δ=8.13 (d, 2H), 8.09 (d, 2H), 7.89-7.98 (m, 2H), 7.66 (br s, 1H), 7.51 (ψt, 3H), 5.95 (d, 1H), 4.12-4.28 (m, 2H), 3.97-4.06 (m, 1H), 3.36-3.49 (m, 2H), 1.9-2.1 (m, 2H), 1.55-1.77 (m, 2H).

The enantiomer separation of 2-{3-[(6-amino-5-nitropyridin-2-yl)amino]piperidin-1-yl}-6-(4-chlorophenyl)pyridine-3-carbonitrile (Example 1) was carried out under the following conditions:

A sample of Example 1 (78 mg) was dissolved in 8 ml of methanol, 8 ml of acetonitrile and 15 ml of tert-butyl methyl ether and chromatographed using a Daicel Chiralpak IA, 5 μm, 250 mm×20 mm column (flow rate: 15 ml/min; detection at 220 nm; injection volume: 500 μl; eluent: tert-butyl methyl ether:methanol (90:10), temperature: 30° C.). Two fractions were isolated:

Example Ent-A-1: 37 mg of product were isolated in >99% ee.

Retention time 4.31 min, spec. rotation: $[α]^{20}_{589}$=−113.0° (c=0.475 g/100 ml of ethanol)

Example Ent-B-1: 33 mg of product were isolated in >98% ee.

Retention time 4.66 min

Example 2

2-(3-{[6-Amino-5-(trifluoroacetyl)pyridin-2-yl]amino}piperidin-1-yl)-6-(2,4-dichlorophenyl)pyridine-3-carbonitrile

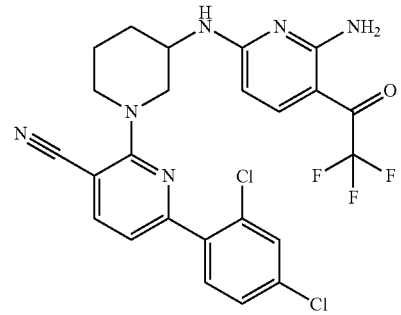 [SMILES: N#Cc1ccc(-c2ccc(Cl)cc2Cl)nc1N1CCCC(Nc2ccc(C(=O)C(F)(F)F)c(N)n2)C1]

29.5 mg (0.1 mmol) of 2-chloro-6-(2,4-dichlorophenyl)pyridine-3-carbonitrile, 30 mg (0.1 mmol) of 1-[2-amino-6-(piperidin-3-ylamino)pyridin-3-yl]-2,2,2-trifluoroethanone hydrochloride (Example 13A) and 0.09 ml (0.52 mmol) of N,N-diisopropylethylamine were initially charged in 1 ml of DMSO. The mixture was heated at 120° C. in a microwave for 30 min. The crude product was purified by means of preparative HPLC (method 13). 35 mg (63% of theory) of the product were obtained in solid form.

LCMS (method 3): $R_t$=3.13 min (m/z=535 (M+H)$^+$).

$^1$H NMR (400 MHz, DMSO-d$_6$): δ=8.50 (br s, 2H), 8.16 (d, 1H), 7.97 (d, 1H), 7.73 (d, 1H), 7.62 (d, 1H), 7.45-7.53 (m, 2H), 7.18 (d, 1H), 5.96 (d, 1H), 4.12-4.25 (m, 2H), 3.99-4.09 (m, 1H), 3.2-3.37 (m, 2H), 1.87-2.08 (m, 2H), 1.5-1.74 (m, 2H).

The enantiomer separation of 2-(3-{[6-amino-5-(trifluoroacetyl)pyridin-2-yl]amino}piperidin-1-yl)-6-(2,4-dichlorophenyl)pyridine-3-carbonitrile (Example 2) was carried out under the following conditions:

A sample of Example 2 (190 mg) was dissolved in 10 ml of 2-propanol and chromatographed using a Daicel Chiralpak AS-H, 5 μm, 250 mm×20 mm column (flow rate: 15 ml/min;

detection at 220 nm; injection volume: 1000 μl; eluent: isohexane:2-propanol (50:50), temperature: 40° C.). Two fractions were isolated:

Example Ent-A-2: 73 mg of product were isolated in >99% ee.

Retention time 6.09 min

Example Ent-B-2: 110 mg of product were isolated in >99% ee.

Retention time 13.38 min

Example 3

2-{3-[(5-Cyanopyridin-2-yl)-amino]piperidin-1-yl}-6-(4-fluorophenyl)pyridine-3-carbonitrile

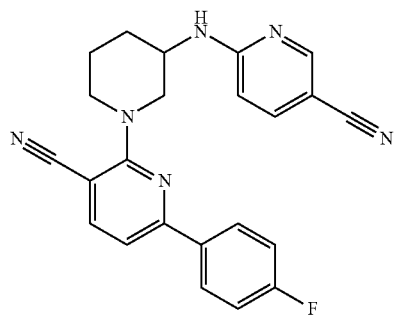 [SMILES: N#Cc1ccc(NC2CCCN(c3nc(-c4ccc(F)cc4)ccc3C#N)C2)nc1]

60 mg (0.26 mmol) of 2-chloro-6-(4-fluorophenyl)pyridine-3-carbonitrile, 77 mg (0.31 mmol) of 6-(piperidin-3-ylamino)pyridine-3-carbonitrile hydrochloride (Example 10A) and 0.225 ml (1.29 mmol) of N,N-diisopropylethylamine were initially charged in 2 ml of DMSO. The mixture was heated at 120° C. in a microwave for 30 min. The crude product was purified by means of preparative HPLC (method 13). 99 mg (50% of theory) of the product were obtained in solid form.

LCMS (method 8): $R_t$=1.40 min (m/z=399 (M+H)$^+$).

$^1$H NMR (400 MHz, DMSO-d$_6$): δ=8.38 (d, 1H), 8.15 (d, 1H), 8.14 (d, 1H), 8.09 (d, 1H), 7.6-7.68 (m, 2H), 7.46 (d, 1H), 7.32 (ψt, 2H), 6.56 (d, 1H), 4.26 (dd, 1H), 4.01-4.14 (m, 2H), 3.33-3.47 (m, 2H), 2.0-2.08 (m, 1H), 1.88-1.97 (m, 1H), 1.55-1.75 (m, 2H).

Example 4

2-(3-{[6-Amino-5-(trifluoroacetyl)pyridin-2-yl]amino}piperidin-1-yl)-6-(4-fluorophenyl)pyridine-3-carbonitrile

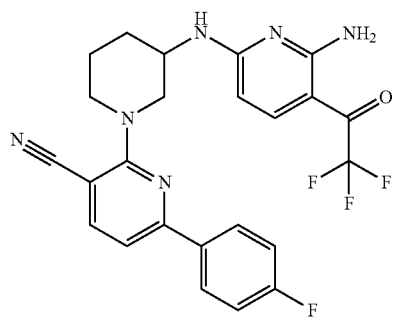 [SMILES: N#Cc1ccc(-c2ccc(F)cc2)nc1N1CCCC(Nc2ccc(C(=O)C(F)(F)F)c(N)n2)C1]

55 mg (0.24 mmol) of 2-chloro-6-(4-fluorophenyl)pyridine-3-carbonitrile, 83 mg (0.28 mmol) of 1-[2-amino-6-(piperidin-3-ylamino)pyridin-3-yl]-2,2,2-trifluoroethanone hydrochloride (Example 13A) and 0.206 ml (1.18 mmol) of N,N-diisopropylethylamine were initially charged in 2 ml of DMSO. The mixture was heated at 120° C. in a microwave for 30 min. The crude product was purified by means of preparative HPLC (method 13). 72 mg (54% of theory) of the product were obtained in solid form.

LCMS (method 8): $R_t$=1.52 min (m/z=485 (M+H)$^+$).

$^1$H NMR (400 MHz, DMSO-d$_6$): δ=8.28 (br s, 1H), 7.86-7.94 (m, 3H), 7.74 (d, 1H), 7.37 (br s, 1H), 7.22-7.30 (m, 2H), 7.05 (t, 2H), 5.74 (d, 1H), 4.02 (m, 1H), 3.93 (d, 1H), 3.76-3.85 (m, 1H), 3.14-3.25 (m, 2H), 1.78-1.86 (m, 1H), 1.67-1.77 (m, 1H), 1.32-1.55 (m, 2H).

Example 5

2-Amino-6-({1-[3-cyano-6-(4-fluorophenyl)pyridin-2-yl]piperidin-3-yl}amino)pyridine-3-carbonitrile

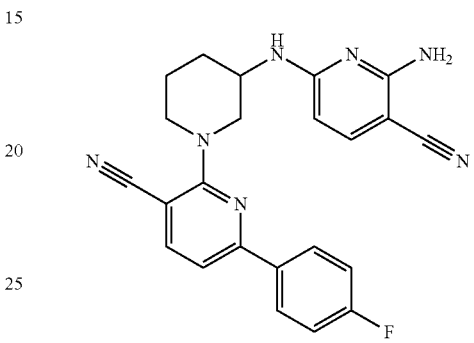

55 mg (0.24 mmol) of 2-chloro-6-(4-fluorophenyl)pyridine-3-carbonitrile, 74 mg (0.28 mmol) of 2-amino-6-(piperidin-3-ylamino)pyridine-3-carbonitrile hydrochloride (Example 11A) and 0.206 ml (1.18 mmol) of N,N-diisopropylethylamine were initially charged in 2 ml of DMSO. The mixture was heated at 120° C. in a microwave for 30 min. The crude product was purified by means of preparative HPLC (method 13). 47 mg (48% of theory) of the product were obtained in solid form.

LCMS (method 3): $R_t$=2.64 min (m/z=414 (M+H)$^+$)

$^1$H NMR (400 MHz, DMSO-d$_6$): δ=8.09-8.17 (m, 3H), 7.47 (d, 1H), 7.26-7.36 (m, 3H), 7.14 (br s, 1H), 6.26 (s, 1H), 5.80 (d, 1H), 4.25 (d, 1H), 4.01-4.12 (m, 2H), 3.17-3.28 (m, 2H), 1.97-2.05 (m, 1H), 1.86-1.96 (m, 1H), 1.62-1.75 (m, 1H), 1.49-1.61 (m, 1H).

Example 6

2-Amino-6-({1-[3-cyano-6-(2,4-dichlorophenyl)pyridin-2-yl]piperidin-3-yl}amino)-pyridine-3-carbonitrile

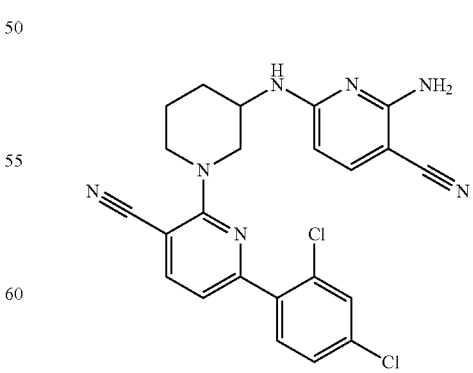

55 mg (0.19 mmol) of 2-chloro-6-(2,4-dichlorophenyl)pyridine-3-carbonitrile, 60.9 mg (0.23 mmol) of 2-amino-6-(piperidin-3-ylamino)pyridine-3-carbonitrile hydrochloride (Example 11A) and 0.169 ml (0.97 mmol) of N,N-diisopropylethylamine were initially charged in 2 ml of DMSO. The mixture was heated at 120° C. in a microwave for 30 min. The crude product was purified by means of preparative HPLC (method 13). 30 mg (33% of theory) of the product were obtained in solid form.

LCMS (method 3): $R_t$=2.90 min (m/z=464 (M+H)$^+$).

$^1$H NMR (400 MHz, DMSO-d$_6$): δ=8.14 (d, 1H), 7.75 (s, 1H), 7.63 (d, 1H), 7.54 (dd, 1H), 7.23 (d, 1H), 7.16 (d, 1H), 7.10 (br s, 1H), 6.22 (br s, 2H), 5.79 (d, 1H), 4.28 (d, 1H), 4.09 (m, 1H), 3.91-4.03 (m, 1H), 3.22 (t, 1H), 3.05 (t, 1H), 1.95-2.04 (m, 1H), 1.82-1.92 (m, 1H), 1.6-1.71 (m, 1H), 1.46-1.58 (m, 1H).

The enantiomer separation of 2-amino-6-({1-[3-cyano-6-(2,4-dichlorophenyl)pyridin-2-yl]-piperidin-3-yl}amino)pyridine-3-carbonitrile (Example 6) was carried out under the following conditions:

A sample of Example 6 (63 mg) was dissolved in 5 ml of ethanol and chromatographed using a Daicel Chiralpak AS-H, 5 μm, 250 mm×20 mm column (flow rate: 15 ml/min; detection at 220 nm; injection volume: 2000 μl; eluent: isohexane:ethanol (50:50), temperature: 40° C.). Two fractions were isolated:

Example Ent-A-6: 25 mg of product were isolated in >99% ee.

Retention time 7.33 min

Example Ent-B-6: 25 mg of product were isolated in >99% ee.

Retention time 15.6 min

Example 7

2-{3-[(5-Cyanopyridin-2-yl)amino]piperidin-1-yl}-6-(2,4-dichlorophenyl)pyridine-3-carbonitrile

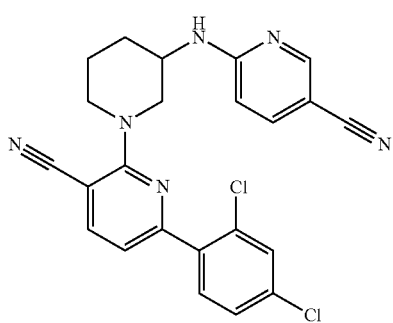 [SMILES: N#Cc1ccc(NC2CCCN(c3nc(-c4ccc(Cl)cc4Cl)ccc3C#N)C2)nc1]

60 mg (0.21 mmol) of 2-chloro-6-(2,4-dichlorophenyl)pyridine-3-carbonitrile, 63 mg (0.25 mmol) of 6-(piperidin-3-ylamino)pyridine-3-carbonitrile hydrochloride (Example 10A) and 0.184 ml (1.06 mmol) of N,N-diisopropylethylamine were initially charged in 2 ml of DMSO. The mixture was heated at 120° C. in a microwave for 30 min. The crude product was purified by means of preparative HPLC (method 13). 61 mg (64% of theory) of the product were obtained in solid form.

LCMS (method 3): $R_t$=3.00 min (m/z=449 (M+H)$^+$).

$^1$H NMR (400 MHz, DMSO-d$_6$): δ=8.32 (d, 1H), 8.12 (d, 1H), 7.74 (d, 1H), 7.52-7.63 (m, 4H), 7.13 (d, 1H), 6.54 (d, 1H), 4.20 (d, 1H), 3.98-4.08 (m, 2H), 3.32-3.42 (m, 2H), 1.98-2.06 (m, 1H), 1.86-1.95 (m, 1H), 1.55-1.73 (m, 2H).

Example 8

Methyl 2-(3-{[6-amino-5-(trifluoroacetyl)pyridin-2-yl]amino}piperidin-1-yl)-6-(2,4-dichlorophenyl)pyridine-3-carboxylate hydrochloride

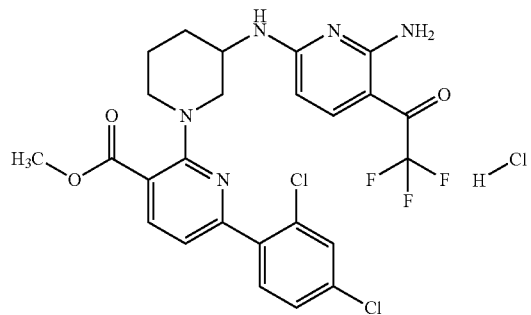

255 mg (0.533 mmol) of methyl 2-chloro-6-(2,4-dichlorophenyl)pyridine-3-carboxylate (Example 16A), 259 mg (0.799 mmol) of 1-[2-amino-6-(piperidin-3-ylamino)pyridin-3-yl]-2,2,2-trifluoroethanone hydrochloride (Example 13A) and 0.56 ml (3.2 mmol) of N,N-diisopropylethylamine were initially charged in 4.5 ml of DMSO. The mixture was heated at 140° C. in a microwave for 45 min. The crude product was purified by means of preparative HPLC (method 10). 28 mg (8% of theory) of the product were obtained in solid form.

LCMS (method 6): $R_t$=2.87 min (m/z=568 (M+H)$^+$).

$^1$H NMR (400 MHz, DMSO-d$_6$): δ=8.50 (br s, 1H), 8.0 (d, 1H), 7.89 (d, 1H), 7.71 (d, 1H), 7.64 (d, 1H), 7.45-7.56 (m, 2H), 7.10 (d, 1H), 5.94 (d, 1H), 4.15 (m, 1H), 3.9-4.0 (m, 1H), 3.84 (s, 3H), 3.58 (m, 1H), 2.96 (dd, 2H), 1.96-2.08 (m, 1H), 1.75-1.86 (m, 1H), 1.57-1.72 (m, 1H), 1.43-1.56 (m, 1H).

Example 9

2-(3-{[6-Amino-5-(trifluoroacetyl)pyridin-2-yl]amino}piperidin-1-yl)-6-(2,4-dichlorophenyl)pyridine-3-carboxylic acid hydrochloride

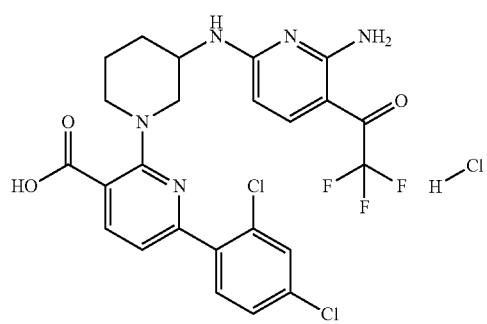

220 mg (0.36 mmol) of methyl 2-(3-{[6-amino-5-(trifluoroacetyl)pyridin-2-yl]amino}piperidin-1-yl)-6-(2,4-dichlorophenyl)pyridine-3-carboxylate hydrochloride (Example 8) were dissolved in 10 ml of 1,2-dimethoxyethane, and 4.4 ml of water were added. Then 43 mg (1.1 mmol) of sodium hydroxide were added and the mixture was stirred at RT for 30 min. For workup, 35 ml of 2 N hydrochloric acid were added and the precipitate which formed was filtered off with suction. 180 mg (75% of theory) of the product were obtained in solid form.

LCMS (method 6): $R_t$=2.42 min (m/z=554 (M+H)$^+$).

$^1$H NMR (400 MHz, DMSO-d$_6$): δ=13.1 (br s, 1H), 8.50 (br s, 1H), 8.02 (d, 1H), 7.9-7.96 (m, 1H), 7.71 (d, 1H), 7.62-7.70 (m, 1H), 7.64 (d, 1H), 7.47-7.55 (m, 2H), 7.11 (d, 1H), 5.95 (d, 1H), 4.11-4.24 (m, 1H), 4.00 (d, 1H), 3.66-3.75 (m, 1H), 2.90 (dd, 2H), 1.98-2.07 (m, 1H), 1.75-1.85 (m, 1H), 1.59-1.74 (m, 1H), 1.42-1.55 (m, 1H).

Example 10

Methyl 2-(3-{[6-amino-5-(trifluoroacetyl)pyridin-2-yl]amino}piperidin-1-yl)-6-(2-methoxyphenyl)pyridine-3-carboxylate hydrochloride

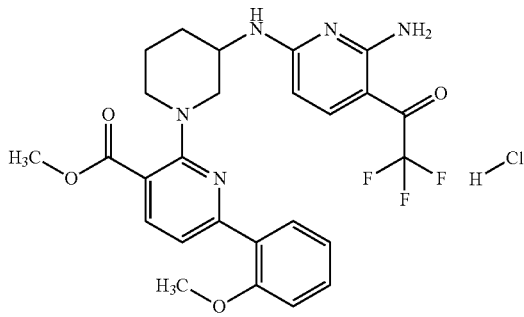

Analogously to the preparation of Example 8, 255 mg (0.84 mmol) of methyl 2-chloro-6-(2-methoxyphenyl)pyridine-3-carboxylate (Example 17A) and 299 mg (0.92 mmol) of 1-[2-amino-6-(piperidin-3-ylamino)pyridin-3-yl]-2,2,2-trifluoroethanone hydrochloride (Example 13A) were used to obtain, after purification of the crude product by means of preparative HPLC (method 10), 275 mg (58% of theory) of the product in solid form.

LCMS (method 6): $R_t$=2.62 min (m/z=530 (M+H)$^+$).

$^1$H NMR (400 MHz, DMSO-d$_6$): δ=8.51 (br s, 1H), 7.9-8.0 (m, 2H), 7.77 (d, 1H), 7.55-7.71 (m, 1H), 7.51 (d, 1H), 7.39 (t, 1H), 7.36 (d, 1H), 7.13 (d, 1H), 7.0 (t, 1H), 5.95 (d, 1H), 4.19 (m, 1H), 3.91-3.98 (m, 1H), 3.83 (s, 3H), 3.55-3.65 (m, 1H), 3.49 (s, 3H), 2.96 (t, 2H), 1.98-2.05 (m, 1H), 1.78-1.85 (m, 1H), 1.6-1.71 (m, 1H), 1.44-1.56 (m, 1H).

Example 11

2-(3-{[6-Amino-5-(trifluoroacetyl)pyridin-2-yl]amino}piperidin-1-yl)-6-(2-methoxyphenyl)pyridine-3-carboxylic acid hydrochloride

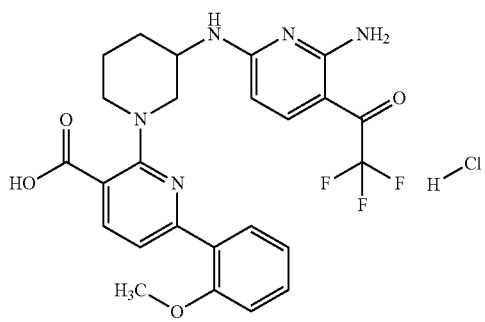

Analogously to the preparation of Example 9, 235 mg (0.42 mmol) of methyl 2-(3-{[6-amino-5-(trifluoroacetyl)pyridin-2-yl]amino}piperidin-1-yl)-6-(2-methoxyphenyl)pyridine-3-carboxylate hydrochloride (Example 10) were used to obtain, by hydrolysis with sodium hydroxide, after purification of the crude product by means of preparative HPLC (method 10), 207 mg (97% of theory) of the product in solid form.

LCMS (method 8): $R_t$=1.28 min (m/z=516 (M+H)$^+$)

$^1$H NMR (400 MHz, DMSO-d$_6$): δ=13.1 (s, br, 1H), 8.51 (s, br, 1H), 7.98 (d, 2H), 7.92 (d, 1H), 7.78 (dd, 1H), 7.68 (s, br, 1H), 7.51 (m, 1H), 7.35-7.44 (m, 2H), 7.13 (d, 1H), 7.02 (t, 1H), 5.95 (d, 1H), 4.20 (m, 1H), 3.94 (m, 1H), 3.83 (s, 3H), 3.69 (m, 1H), 2.87-2.98 (m, 2H), 1.98-2.07 (m, 1H), 1.76-1.85 (m, 1H), 1.6-1.75 (m, 1H), 1.42-1.54 (m, 1H).

General Experimental Description for Amide Couplings:

0.117 mmol of the particular amine is initially charged in 3 ml of DMF, and admixed successively with 0.125 mmol of HATU, 0.25 mmol of N,N-diisopropylethylamine and 0.083 mmol of the acid (Example 9 and Example 11). The mixture is stirred at RT for 16 h. After purification by means of preparative HPLC (method 13), the products are obtained in solid form.

The general experimental description for amide couplings was used to prepare the following compounds:

| Ex. | Structure | Characterization: |
|---|---|---|
| 12 | 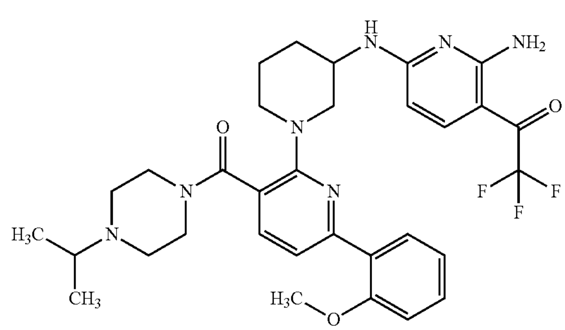 [SMILES: COc1ccccc1-c1ccc(C(=O)N2CCN(C(C)C)CC2)c(N2CCCC(Nc3ccc(C(=O)C(F)(F)F)c(N)n3)C2)n1] | LC-MS (method 8): $R_t$ = 1.11 min, (m/z = 624 (M – H)$^+$) |

| Ex. | Structure | Characterization: |
|---|---|---|
| 13 | 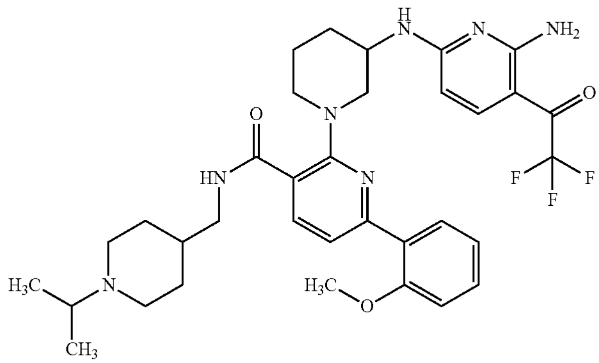 [SMILES: COc1ccccc1-c1ccc(C(=O)NCC2CCN(C(C)C)CC2)c(N2CCCC(Nc3ccc(C(=O)C(F)(F)F)c(N)n3)C2)n1] | LC-MS (method 3): R$_t$ = 1.83 min, (m/z = 654 (M + H)$^+$) |
| 14 | 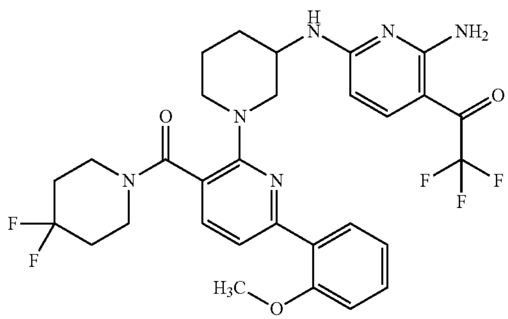 [SMILES: COc1ccccc1-c1ccc(C(=O)N2CCC(F)(F)CC2)c(N2CCCC(Nc3ccc(C(=O)C(F)(F)F)c(N)n3)C2)n1] | LC-MS (method 8): R$_t$ = 1.49 min, (m/z = 619 (M + H)$^+$) |
| 15 | 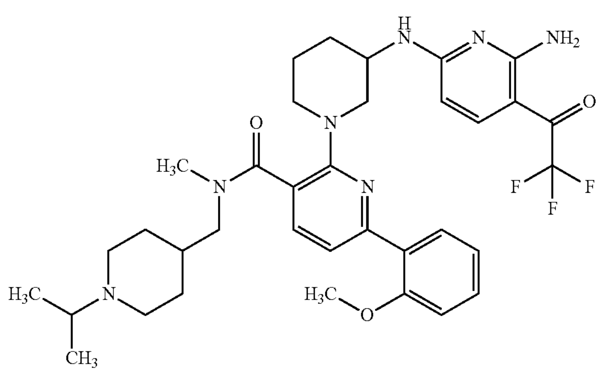 [SMILES: COc1ccccc1-c1ccc(C(=O)N(C)CC2CCN(C(C)C)CC2)c(N2CCCC(Nc3ccc(C(=O)C(F)(F)F)c(N)n3)C2)n1] | LC-MS (method 6): R$_t$ = 1.56 min, (m/z = 668 (M + H)$^+$) |
| 16 | 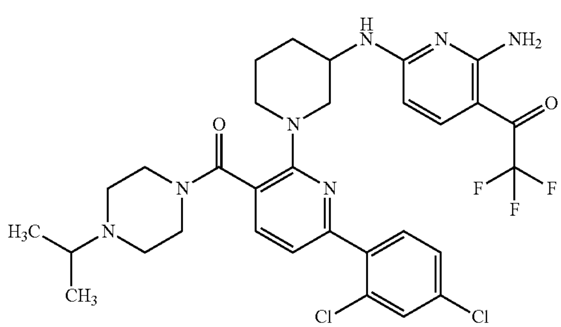 [SMILES: CC(C)N1CCN(C(=O)c2ccc(-c3ccc(Cl)cc3Cl)nc2N2CCCC(Nc3ccc(C(=O)C(F)(F)F)c(N)n3)C2)CC1] | LC-MS (method 6): R$_t$ = 1.63 min, (m/z = 664 (M − H)$^+$) |

| Ex. | Structure | Characterization: |
|---|---|---|
| 17 | 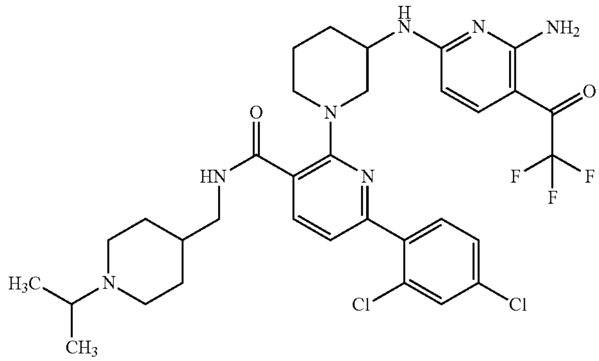 [SMILES: CC(C)N1CCC(CNC(=O)c2ccc(-c3ccc(Cl)cc3Cl)nc2N2CCCC(Nc3ccc(C(=O)C(F)(F)F)c(N)n3)C2)CC1] | LC-MS (method 8): $R_t$ = 1.27 min, (m/z = 691 (M − H)$^+$) |
| 18 | 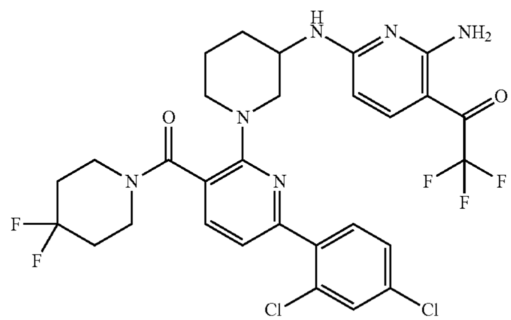 [SMILES: Nc1nc(NC2CCCN(c3nc(-c4ccc(Cl)cc4Cl)ccc3C(=O)N3CCC(F)(F)CC3)C2)ccc1C(=O)C(F)(F)F] | LC-MS (method 6): $R_t$ = 2.76 min, (m/z = 657 (M + H)$^+$) |
| 19 | 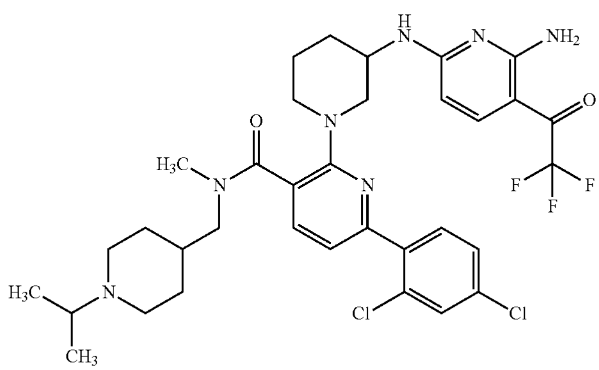 [SMILES: CC(C)N1CCC(CN(C)C(=O)c2ccc(-c3ccc(Cl)cc3Cl)nc2N2CCCC(Nc3ccc(C(=O)C(F)(F)F)c(N)n3)C2)CC1] | LC-MS (method 8): $R_t$ = 1.27 min, (m/z = 706 (M + H)$^+$) |

The enantiomer separation of 1-[2-amino-6-({1-[6-(2-methoxyphenyl)-3-{[4-(propan-2-yl)-piperazin-1-yl]carbonyl}pyridin-2-yl]piperidin-3-yl}amino)pyridin-3-yl]-2,2,2-trifluoroethanone (Example 12) was carried out under the following conditions:

A sample of Example 12 (24 mg) was dissolved in 2 ml of 2-propanol and chromatographed using a Daicel Chiralpak AD-H, 5 µm, 250 mm×20 mm column (flow rate: 15 ml/min; detection at 220 nm; injection volume: 500 µl; eluent: isohexane:2-propanol with 0.2% diethylamine (60:40), temperature: 30° C.). Two fractions were isolated:

Example Ent-A-12: 15 mg of product were isolated in >99% ee.

Retention time 5.26 min, spec. rotation: [α]$^{20}_{589}$=−173.7° (c=0.37 g/100 ml of ethanol)

Example Ent-B-12: 9 mg of product were isolated in >99% ee.

Retention time 6.30 min

The enantiomer separation of 2-(3-{[6-amino-5-(trifluoroacetyl)pyridin-2-yl]amino}-piperidin-1-yl)-6-(2-methoxyphenyl)-N-{[1-(propan-2-yl)piperidin-4-yl]methyl}pyridine-3-carboxamide (Example 13) was carried out under the following conditions:

A sample of Example 13 (28 mg) was dissolved in 1 ml of ethanol and chromatographed using a Daicel Chiralpak AD-H, 5 µm, 250 mm×20 mm column (flow rate: 15 ml/min; detection at 220 nm; injection volume: 500 µl; eluent: isohexane:ethanol with 0.2% diethylamine (60:40), temperature: 30° C.). Two fractions were isolated:

Example Ent-A-13: 6 mg of product were isolated in >99% ee.

Retention time 4.57 min

Example Ent-B-13: 12 mg of product were isolated in >99% ee.

Retention time 6.66 min, spec. rotation: [α]$^{20}_{589}$=−103.7° (c=0.375 g/100 ml of ethanol)

The enantiomer separation of 1-{2-amino-6-[(1-{3-[(4,4-difluoropiperidin-1-yl)carbonyl]-6-(2-methoxyphenyl)pyridin-2-yl}piperidin-3-yl)amino]pyridin-3-yl}-2,2,2-trifluoroethanone (Example 14) was carried out under the following conditions:

A sample of Example 14 (28 mg) was dissolved in 2 ml of 2-propanol and chromatographed using a Daicel Chiralpak AD-H, 5 µm, 250 mm×20 mm column (flow rate: 15 ml/min; detection at 220 nm; injection volume: 500 µl; eluent: isohexane:2-propanol with 0.2% diethylamine (60:40), temperature: 30° C.). Two fractions were isolated:

Example Ent-A-14: 15 mg of product were isolated in >99% ee.

Retention time 5.96 min, spec. rotation: $[\alpha]^{20}_{589}=-166.7°$ (c=0.38 g/100 ml of ethanol)

Example Ent-B-14: 11 mg of product were isolated in >99% ee.

Retention time 7.25 min

Example 20

2-(3-{[6-Amino-5-(trifluoroacetyl)pyridin-2-yl]amino}piperidin-1-yl)-6-(2-chlorophenyl)-4-(trifluoromethyl)pyridine-3-carbonitrile

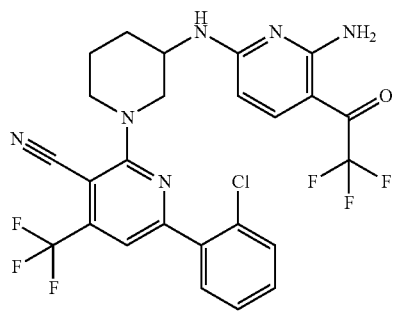 [SMILES: N#Cc1c(C(F)(F)F)cc(-c2ccccc2Cl)nc1N1CCCC(Nc2ccc(C(=O)C(F)(F)F)c(N)n2)C1]

70 mg (0.221 mmol) of 2-chloro-6-(2-chlorophenyl)-4-(trifluoromethyl)pyridine-3-carbonitrile, 65 mg (0.221 mmol) of 1-[2-amino-6-(piperidin-3-ylamino)pyridin-3-yl]-2,2,2-trifluoroethanone hydrochloride (Example 13A) and 0.192 ml (1.1 mmol) of N,N-diisopropylethylamine were initially charged in 2 ml of DMSO. The reaction mixture was irradiated in a microwave reactor at 120° C. for 30 min. The reaction mixture was purified by means of preparative HPLC (method 13). This gave 86 mg (68% of theory) of the product.

LCMS (method 6): $R_f$=2.84 min (m/z=569 (M+H)$^+$).

$^1$H NMR (400 MHz, DMSO-d$_6$): δ=8.49 (br s, 1H), 7.90 (d, 1H), 7.69 (dd, 1H), 7.59 (d, 1H), 7.42-7.58 (m, 5H), 5.91 (d, 1H), 4.11-4.22 (m, 2H), 3.92-4.01 (m, 1H), 3.48-3.64 (m, 2H), 1.96-2.09 (m, 2H), 1.58-1.75 (m, 2H).

The enantiomer separation of 2-(3-{[6-amino-5-(trifluoroacetyl)pyridin-2-yl]amino}piperidin-1-yl)-6-(2-chlorophenyl)-4-(trifluoromethyl)pyridine-3-carbonitrile (Example 20) was carried out under the following conditions:

A sample of Example 20 (75 mg) was dissolved in 2 ml of ethanol and chromatographed using a Daicel Chiralpak AS-H, 5 µm, 250 mm×20 mm column (flow rate: 15 ml/min; detection at 220 nm; injection volume: 1000 µl; eluent: isohexane:ethanol (70:30), temperature: 40° C.). Two fractions were isolated:

Example Ent-A-20: 28 mg of product were isolated in >99% ee.

Retention time 4.23 min, spec. rotation: $[\alpha]^{20}_{589}=+318.4°$ (c=0.622 g/100 ml of ethanol)

Example Ent-B-20: 46 mg of product were isolated in >99% ee.

Retention time 6.34 min

Example 21

2-(3-{[6-Amino-5-(trifluoroacetyl)pyridin-2-yl]amino}piperidin-1-yl)-6-(4-fluorophenyl)-4-(trifluoromethyl)pyridine-3-carbonitrile

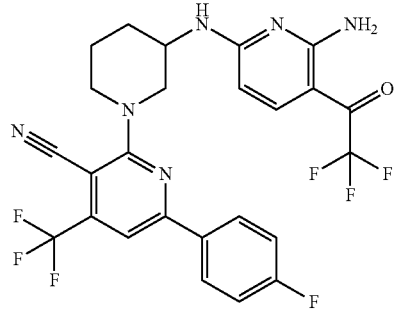 [SMILES: N#Cc1c(C(F)(F)F)cc(-c2ccc(F)cc2)nc1N1CCCC(Nc2ccc(C(=O)C(F)(F)F)c(N)n2)C1]

Analogously to the preparation of Example 20, 60 mg (0.2 mmol) of 2-chloro-6-(4-fluorophenyl)-4-(trifluoromethyl)pyridine-3-carbonitrile and 70.4 mg (0.24 mmol) of 1-[2-amino-6-(piperidin-3-ylamino)pyridin-3-yl]-2,2,2-trifluoroethanone hydrochloride (Example 13A) were used to obtain, after separation by means of preparative HPLC (method 13), 92 mg (83% of theory) of the product in solid form.

LCMS (method 8): $R_f$=1.61 min (m/z=553 (M+H)$^+$).

$^1$H NMR (400 MHz, DMSO-d$_6$): δ=8.50 (br s, 1H), 8.20-8.28 (m, 2H), 7.90 (d, 1H), 7.78 (s, 1H), 7.58 (br s, 1H), 7.45 (d, 1H), 7.30 (ψt, 2H), 5.90 (d, 1H), 4.17-4.28 (m, 1H), 4.07 (d, 1H), 3.88-3.97 (m, 1H), 3.75-3.83 (m, 1H), 3.59-3.68 (m, 1H), 1.97-2.09 (m, 2H), 1.62-1.77 (m, 2H).

The enantiomer separation of 2-(3-{[6-amino-5-(trifluoroacetyl)pyridin-2-yl]amino}piperidin-1-yl)-6-(4-fluorophenyl)-4-(trifluoromethyl)pyridine-3-carbonitrile (Example 21) was carried out under the following conditions:

A sample of Example 21 (84 mg) was dissolved in 20 ml of isohexane:ethanol (4:1) and chromatographed using a Daicel Chiralpak AS-H, 5 µm, 250 mm×20 mm column (flow rate: 20 ml/min; detection at 230 nm; injection volume: 20 000 µl; eluent:

isohexane:ethanol (80:20), temperature: 24° C.). Two fractions were isolated:

Example Ent-A-21: 39 mg of product were isolated in >99% ee.

Retention time 4.52 min, spec. rotation: $[\alpha]^{20}_{589}=+327.6°$ (c=0.5905 g/100 ml of ethanol)

Example Ent-B-21: 24 mg of product were isolated in >99% ee.

Retention time 6.62 min

Example 22

2-(3-{[6-Amino-5-(trifluoroacetyl)pyridin-2-yl]amino}piperidin-1-yl)-6-(3-chlorophenyl)-4-(trifluoromethyl)pyridine-3-carbonitrile

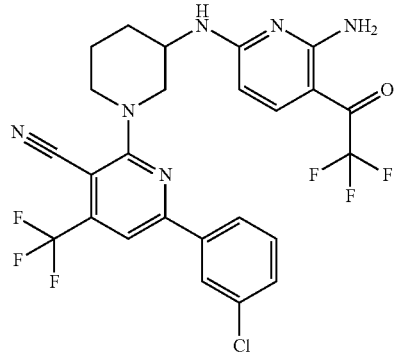 [SMILES: N#Cc1c(C(F)(F)F)cc(-c2cccc(Cl)c2)nc1N1CCCC(Nc2ccc(C(=O)C(F)(F)F)c(N)n2)C1]

Analogously to the preparation of Example 20, 60 mg (0.19 mmol) of 2-chloro-6-(3-chlorophenyl)-4-(trifluoromethyl)pyridine-3-carbonitrile and 66.8 mg (0.23 mmol) of 1-[2-amino-6-(piperidin-3-ylamino)pyridin-3-yl]-2,2,2-trifluoroethanone hydrochloride (Example 13A) were used to obtain, after separation by means of preparative HPLC (method 13), 96 mg (89% of theory) of the product in solid form.

LCMS (method 8): $R_t$=1.67 min (m/z=569 (M+H)$^+$).

$^1$H NMR (400 MHz, DMSO-d$_6$): δ=8.49 (br s, 1H), 8.23 (t, 1H), 8.13 (d, 1H), 7.90 (d, 1H), 7.85 (s, 1H), 7.59 (d, 1H), 7.56 (br s, 1H), 7.51 (d, 1H), 7.46 (m, 1H), 5.89 (d, 1H), 4.22 (m, 1H), 4.13 (d, 1H), 3.9-3.99 (m, 1H), 3.72 (dd, 1H), 3.58-3.67 (m, 1H), 2.0-2.12 (m, 2H), 1.61-1.78 (m, 2H).

The enantiomer separation of 2-(3-{[6-amino-5-(trifluoroacetyl)pyridin-2-yl]amino}piperidin-1-yl)-6-(3-chlorophenyl)-4-(trifluoromethyl)pyridine-3-carbonitrile (Example 22) was carried out under the following conditions:

A sample of Example 22 (83 mg) was dissolved in 20 ml of isohexane:ethanol (4:1) and chromatographed using a Daicel Chiralpak AS-H, 5 μm, 250 mm×20 mm column (flow rate: 20 ml/min; detection at 230 nm; injection volume: 4500 μl; eluent: isohexane:ethanol (80:20), temperature: 24° C.). Two fractions were isolated:

Example Ent-A-22: 26 mg of product were isolated in >99% ee.

Retention time 4.54 min, spec. rotation: $[α]^{20}_{589}$=+328.2° (c=0.4645 g/100 ml of ethanol)

Example Ent-B-22: 42 mg of product were isolated in >99% ee.

Retention time 7.15 min

Example 23

6-(2-Chlorophenyl)-2-{3-[(5-cyanopyridin-2-yl)amino]piperidin-1-yl}-4-(trifluoromethyl)-pyridine-3-carbonitrile

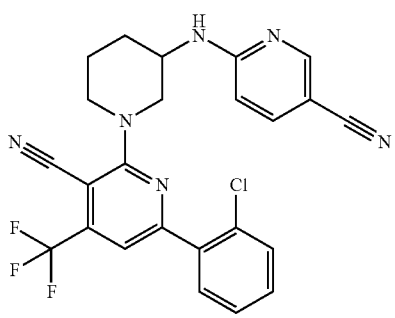 [SMILES: N#Cc1ccc(NC2CCCN(c3nc(-c4ccccc4Cl)cc(C(F)(F)F)c3C#N)C2)nc1]

Analogously to the preparation of Example 20, 60 mg (0.19 mmol) of 2-chloro-6-(2-chlorophenyl)-4-(trifluoromethyl)pyridine-3-carbonitrile and 47 mg (0.19 mmol) of 6-(piperidin-3-ylamino)pyridine-3-carbonitrile hydrochloride (Example 10A) were used to obtain, after separation by means of preparative HPLC (method 13), 61 mg (67% of theory) of the product in solid form.

LCMS (method 8): $R_t$=1.53 min (m/z=483 (M+H)$^+$).

$^1$H NMR (400 MHz, DMSO-d$_6$): δ=8.31 (d, 1H), 7.67 (dd, 1H), 7.45-7.64 (m, 6H), 6.51 (d, 1H), 4.15 (d, 1H), 3.91-4.07 (m, 2H), 3.52-3.65 (m, 2H), 1.94-2.07 (m, 2H), 1.61-1.75 (m, 2H).

Example 24

2-{3-[(5-Cyanopyridin-2-yl)amino]piperidin-1-yl}-6-(4-fluorophenyl)-4-(trifluoromethyl)-pyridine-3-carbonitrile

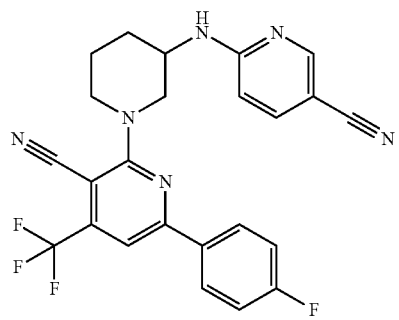 [SMILES: N#Cc1ccc(NC2CCCN(c3nc(-c4ccc(F)cc4)cc(C(F)(F)F)c3C#N)C2)nc1]

Analogously to the preparation of Example 20, 60 mg (0.2 mmol) of 2-chloro-6-(4-fluorophenyl)-4-(trifluoromethyl)pyridine-3-carbonitrile and 59.5 mg (0.24 mmol) of 6-(piperidin-3-ylamino)pyridine-3-carbonitrile hydrochloride (Example 10A) were used to obtain, after separation by means of preparative HPLC (method 13), 61 mg (66% of theory) of the product in solid form.

LCMS (method 8): $R_t$=1.5 min (m/z=467 (M+H)$^+$).

$^1$H NMR (400 MHz, DMSO-d$_6$): δ=8.38 (d, 1H), 8.23-8.29 (m, 2H), 7.76 (s, 1H), 7.57-7.65 (m, 2H), 7.36 (ψt, 2H), 6.52 (d, 1H), 4.19 (dd, 1H), 4.09 (m, 1H), 3.93-4.01 (m, 1H), 3.57-3.71 (m, 2H), 1.92-2.09 (m, 2H), 1.61-1.78 (m, 2H).

Example 25

6-(4-Chlorophenyl)-2-{3-[(5-cyanopyridin-2-yl)amino]piperidin-1-yl}-4-(trifluoromethyl)-pyridine-3-carbonitrile

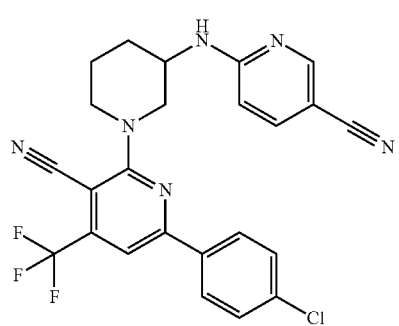 [SMILES: N#Cc1ccc(NC2CCCN(c3nc(-c4ccc(Cl)cc4)cc(C(F)(F)F)c3C#N)C2)nc1]

Analogously to the preparation of Example 20, 60 mg (0.19 mmol) of 2-chloro-6-(4-chlorophenyl)-4-(trifluoromethyl)pyridine-3-carbonitrile and 56 mg (0.23 mmol) of 6-(piperidin-3-ylamino)pyridine-3-carbonitrile hydrochloride (Example 10A) were used to obtain, after separation by means of preparative HPLC (method 13), 46 mg (50% of theory) of the product in solid form.

LCMS (method 8): $R_t$=1.57 min (m/z=483 (M+H)$^+$).

$^1$H NMR (400 MHz, DMSO-d$_6$): δ=8.38 (d, 1H), 8.21 (d, 2H), 7.78 (s, 1H), 7.55-7.65 (m, 4H), 6.52 (d, 1H), 4.18 (d, 1H), 4.09 (m, 1H), 3.92-4.01 (m, 1H), 3.59-3.72 (m, 2H), 1.96-2.09 (m, 2H), 1.63-1.76 (m, 2H).

Example 26

2-{3-[(6-Amino-5-cyanopyridin-2-yl)amino]piperidin-1-yl}-6-(2-chlorophenyl)-4-(trifluoromethyl)pyridine-3-carbonitrile

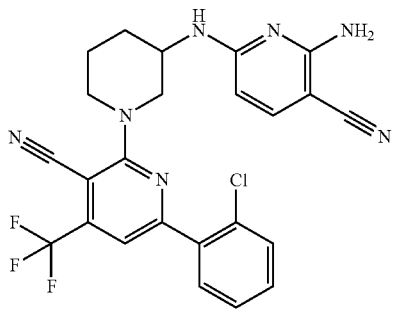 [SMILES: N#Cc1ccc(NC2CCCN(c3nc(-c4ccccc4Cl)cc(C(F)(F)F)c3C#N)C2)nc1N]

Analogously to the preparation of Example 20, 60 mg (0.19 mmol) of 2-chloro-6-(2-chlorophenyl)-4-(trifluoromethyl)pyridine-3-carbonitrile and 49.5 mg (0.19 mmol) of 2-amino-6-(piperidin-3-ylamino)pyridine-3-carbonitrile hydrochloride (Example 11A) were used to obtain, after separation by means of preparative HPLC (method 13), 94 mg (99% of theory) of the product in solid form.

LCMS (method 3): $R_t$=2.87 min (m/z=498 (M+H)$^+$).

$^1$H NMR (400 MHz, DMSO-d$_6$): δ=7.69 (dd, 1H), 7.61 (dd, 1H), 7.54 (dd, 1H), 7.45-7.52 (m, 2H), 7.22 (d, 1H), 7.10 (br s, 1H), 6.21 (s, 2H), 5.75-5.8 (m, 1H), 4.24 (d, 1H), 3.91-4.10 (m, 2H), 3.33-3.45 (m, 2H), 1.9-2.05 (m, 2H), 1.5-1.73 (m, 2H).

The enantiomer separation of 2-{3-[(6-amino-5-cyanopyridin-2-yl)amino]piperidin-1-yl}-6-(2-chlorophenyl)-4-(trifluoromethyl)pyridine-3-carbonitrile (Example 26) was carried out under the following conditions:

A sample of Example 26 (83 mg) was dissolved in 20 ml of isohexane:ethanol (3:2) and chromatographed using a Daicel Chiralpak AS-H, 5 μm, 250 mm×20 mm column (flow rate: 20 ml/min; detection at 230 nm; injection volume: 4500 μl; eluent: isohexane:ethanol (70:30), temperature: 24° C.). Two fractions were isolated:

Example Ent-A-26: 26 mg of product were isolated in >99% ee.

Retention time 7.97 min, spec. rotation: $[α]^{20}_{589}$=+208° (c=0.230 g/100 ml of ethanol)

Example Ent-B-26: 26 mg of product were isolated in >99% ee.

Retention time 13.57 min

Example 27

2-{3-[(6-Amino-5-cyanopyridin-2-yl)amino]piperidin-1-yl}-6-(4-fluorophenyl)-4-(trifluoromethyl)pyridine-3-carbonitrile

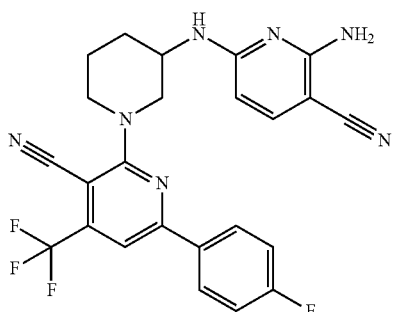

Analogously to the preparation of Example 20, 60 mg (0.2 mmol) of 2-chloro-6-(4-fluorophenyl)-4-(trifluoromethyl)pyridine-3-carbonitrile and 62.6 mg (0.24 mmol) of 2-amino-6-(piperidin-3-ylamino)pyridine-3-carbonitrile hydrochloride (Example 11A) were used to obtain, after separation by means of preparative HPLC (method 13), 90 mg (94% of theory) of the product in solid form.

LCMS (method 3): $R_t$=2.83 min (m/z=482 (M+H)$^+$).

$^1$H NMR (400 MHz, DMSO-d$_6$): δ=8.21-8.28 (m, 1H), 7.78 (s, 1H), 7.35 (ψt, 2H), 7.27 (d, 1H), 7.12 (d, 1H), 6.25 (br s, 2H), 5.77 (d, 2H), 4.19 (d, 1H), 3.98-4.1 (d, 2H), 3.42-3.58 (m, 2H), 1.92-2.07 (m, 2H), 1.56-1.78 (m, 2H).

B) Assessment of Physiological Efficacy

The suitability of the inventive compounds for treatment of haematological disorders can be demonstrated in the following assay systems:

In Vitro Assay

The inhibitory activity of active substances is determined in a biochemical assay. The ingredients required for this purpose are mixed in a black 384-well microtitre plate with transparent base (from Greiner, catalogue number 781092). The ingredients required for each well of the 384-well microtitre plate are 5 nM GSK3β (from Upstate, catalogue number 14-306), 40 μM GSK3β substrate GSM (sequence H-RRRPASVPPSPSLSRHS-(pS)-HQRR, from Upstate, catalogue number 2-533), 30 μM nicotinamide adenine dinucleotide NADH (Roche Diagnostics, catalogue number 10107735), 50 μM adenosine triphosphate ATP (from Sigma, catalogue number A7966), 2 mM phosphoenolpyruvate (from Roche, catalogue number 128112), and approx. 1 U/ml pyruvate kinase and approx. 1 U/ml lactate dehydrogenase, which are present together in a stock formulation (from Roche, catalogue number 10737291001, suspension with approx. 450 U/ml pyruvate kinase activity, approx. 450 U/ml lactate dehydrogenase activity in 3.2 mM ammonium sulphate solution pH 6). 1 unit of pyruvate kinase converts 1 μmol of phosphoenolpyruvate to pyruvate per minute at pH 7.6 and 37° C., and 1 unit of lactate dehydrogenase reduces 1 μmol of pyruvate to lactate per minute at pH 7.5 and 37° C. The reaction buffer required, in which the biochemical reaction proceeds, consists of 50 mM Trizma hydrochloride Tris-HCl pH: 7.5 (from Sigma, catalogue number T3253), 5 mM magnesium chloride MgCl$_2$ (from Sigma, catalogue number M8266), 0.2 mM DL-dithiothreitol DTT (from Sigma, catalogue number D9779), 2 mM ethylenediamine ether tetraacid EDTA (from Sigma, catalogue number E6758), 0.01% Triton X-100 (from Sigma, catalogue number T8787) and 0.05% bovine serum albumin BSA (from Sigma, catalogue number B4287).

Active substances are dissolved in dimethyl sulphoxide DMSO (from Sigma, catalogue number D8418) in a concentration of 10 mM. Active substances are added in serial concentrations of 10 μM, 1 μM, 0.1 μM, 0.01 μM, 0.001 μM, 0.0001 μM, 0.00001 μM, 0.000001 μM to the mixtures of the biochemical reaction. As control, dimethyl sulphoxide is added instead of substance in a final concentration of 0.1%.

The reaction is incubated at 30° C. for 2 hours and then the resulting fluorescence is measured in a Tecan Safire-XFLUOR4 instrument, version V4.50 (serial number 12901300283) with the specifications: measurement mode—fluorescence measured from below, excitation wavelength 340 nm, emission wavelength 465 nm, excitation slit width 5 nm, emission slit width 5 nm, gain mode 120, delay 0 μs, number of light flashes per measurement 3, and an integration time of 40 μs.

The GSK3β activity is measured in fluorescence units, equating the values of uninhibited kinase to 100% and those of completely inhibited kinase to 0%. The activity of the active substances is calculated in relation to these 0% and 100%.

Table A shows $IC_{50}$ values which have been determined in the assay described above:

TABLE A

| Example No. | $IC_{50}$ [nM] |
|---|---|
| Ent-B-2 | 5.04 |
| 6 | 26 |
| 7 | 12 |
| Ent-B-12 | 6.3 |

CD34+ Proliferation Assays for Testing of GSK3β Inhibitors

Adult haematopoietic stem cells are characterized by the specific expression of membrane-associated proteins. These surface markers are provided with an appropriate number according to their molecular weight. This class also includes the molecule which is referred to as CD34 and which serves for the identification, characterization and isolation of adult haematopoietic stem cells. These stem cells can be isolated from bone marrow, peripheral blood or umbilical cord blood. These cells have limited viability in in vitro cultures but can be stimulated to proliferation and differentiation by a wide variety of additions to the culture medium. CD34-positive cells are used here in order to test the influence of substances on the activity of glycogen synthase kinase 3. For this purpose, in a first step, mononuclear cells are isolated from umbilical cord blood by differential centrifugation steps.

For this purpose, umbilical cord blood is diluted 1:4 with phosphate-buffered saline solution. 50 millilitre centrifugation vessels are charged with 17 millilitres of Ficoll (density 1.077, Ficoll Paque Plus; Pharmacia, catalogue number 17-1440-02). 30 millilitres of the 1:4 diluted umbilical cord blood are layered thereon and then centrifuged at 400×g at room temperature for 30 minutes. The brakes of the centrifuge are disengaged during this. Owing to the centrifugation, the mononuclear cells collect in the interphase. The latter is removed with the aid of a 30 millilitre pipette and transferred into a new 50 millilitre centrifugation vessel, and the volume is then made up to 30 ml with phosphate-buffered saline solution. These cells are centrifuged at 300×g with the brake engaged at room temperature for 10 minutes. The supernatant is discarded and the resulting cell pellet is resuspended in 30 millilitres of phosphate-buffered saline solution. These cells are again centrifuged at 200×g with brake engaged at 20° C. for 15 minutes.

To isolate the CD34-positive cells from the enriched mononuclear cells resuspended in a concentration of 1×10⁸ cells per 300 microlitres of MACS buffer (0.5% endotoxin-free bovine serum albumin in phosphate-buffered saline solution). 100 microlitres of FCR blocking reagent (Miltenyi Biotec, catalogue number 130-046-702) and 100 microlitres of CD34 microbeads (Miltenyi Biotec, catalogue number 130-046-702) are added. This suspension is incubated at 4° C. for 30 minutes. The cells are then diluted with 20 times the volume of MACS buffer and centrifuged at 300×g for 10 minutes. The supernatant is discarded and the cells are resuspended in 500 microlitres of MACS buffer. The cells treated in this way are loaded onto an LS column (Miltenyi Biotec, catalogue number 130-042-401) and purified using a Midi MACS magnet (Miltenyi Biotec, catalogue number 130-042-303).

The number of CD34-positive cells is carried out by counting the cells using a Neubauer chamber. The purity of the cells is determined by standard protocols using the fluorescent activated cell sorting method (Becton Dickinson, BD FACS™ Sample Prep Assistant SPAII Upgrade Kit, catalogue number 337642).

To determine the influence of modulating the GSK3 activity, CD34-positive cells are incubated in a 96-well microtitre plate at 37° C. and 5% carbon dioxide for 7 days and then the proliferation rates are determined on the basis of the cell counts.

For this purpose, 5000 CD34-positive cells are taken up in 100 microlitres of IMDM medium (Life Technology, catalogue number 12440-046), 10% foetal calf serum (Life Technology, catalogue number 10082-139) and 20 nanograms per millilitre of stem cell factor (R&D, catalogue number 255-SC-010) in each well of a 96 U-bottom well microtitre plate (Greiner Bio-One, catalogue number 650 180). In addition, the cells are also mixed with various concentrations of substances dissolved in dimethyl sulphoxide (Sigma Aldrich, catalogue number D5879-1L). This is done by providing 4 wells in each case with the stated cell count of 5000 CD34-positive cells per well with 10 micromol, 4 wells with 5 micromol, 4 wells with 2.5 micromol, 4 wells with 1.25 micromol, 4 wells with 0.625 micromol, 4 wells with 0.3125 micromol, 4 wells with 0.156 micromol, 4 wells with 0.078 micromol, and as control 4 wells with 0.1% dimethyl sulphoxide as final concentration.

These cells treated in this way are incubated in a cell culture incubator at 37° C. and 5% carbon dioxide for 7 days. The proliferation rate is determined by again counting the cells using a Neubauer counting chamber, setting the cells provided only with the stem cell factor as 100% value, and all other values being related to this value.

In Vivo Assay

The in vivo effect of the inventive compounds is examined using 6-week-old male C57BL/6 mice (Charles River, Sulzfeld, Germany) weighing 18-22 g. These animals are kept appropriately for the species with 12-hour light and dark cycles under constant climatic conditions and with water and mouse feed ad libitum. The concentrations of chemotherapeutics used are administered to the animals in accordance with the manufacturers' statements by intraperitoneal (i.p.) injections in the caudal third of the abdomen. The same procedure is applied to the substances relevant to the invention. Blood samples are taken from the retrobulbar venous plexus using Pasteur pipettes. The number of neutrophilic granulocytes is determined in a fully automated manner using flow cytometry systems.

CYP Inhibition Test

The ability of substances to inhibit CYP1A2, CYP2C8, CYP2C9, CYP2D6 and CYP3A4 in humans is examined using pooled human liver microsomes as the enzyme source in the presence of standard substrates (vide infra) which form CYP isoform-specific metabolites. The inhibitory effects are examined at six different concentrations of the test compounds (1.5, 3.1, 6.3, 12.5, 25 and 50 μM) and compared to the extent of the CYP isoform-specific metabolite formation of the standard substrates in the absence of the test compounds, and the corresponding $IC_{50}$ values are calculated. A standard inhibitor which specifically inhibits a single CYP isoform serves as control for the results obtained.

Procedure:

The incubation of phenacetin, amodiaquine, diclofenac, dextromethorphan or midazolam with human liver microsomes in the presence of in each case six different concentrations of a test compound (as potential inhibitor) is carried out on a workstation (Tecan, Genesis, Crailsheim, Germany). Standard incubation mixtures comprise 1.3 mM NADP, 3.3 mM $MgCl_2 \times 6\ H_2O$, 3.3 mM glucose 6-phosphate, glucose 6-phosphate dehydrogenase (0.4 U/ml) and 100 mM phosphate buffer (pH 7.4) in a total volume of 200 μl. Test compounds are preferably dissolved in acetonitrile. 96-Well plates are incubated for a defined period of time at 37° C. with pooled human liver microsomes. The reactions are stopped by addition of 100 µl of acetonitrile comprising a suitable internal standard. Precipitated proteins are removed by centrifugation, and the supernatants are combined and analysed by LC-MS/MS.

Determination of the Solubility

Reagents Required:

PBS buffer pH 6.5: 61.86 g of sodium chloride p.a. (for example from Merck, Art. No. 1.06404.1000), 39.54 g of sodium dihydrogenphosphate p.a. (for example from Merck, Art. No. 1.06346.1000) and 83.35 g of 1 N sodium hydroxide solution (for example from Bernd Kraft GmbH, Art. No. 01030.4000) are weighed out into a 1 litre standard flask and made up to the mark with water, and the mixture is stirred for about 1 hour. 500 ml of this solution are added to a 5 litre standard flask and made up to the mark with water. The pH is adjusted to 6.5 using 1 N sodium hydroxide solution.

dimethyl sulphoxide (for example from Baker, Art. No. 7157.2500)

distilled water

Chromasolv acetonitrile (for example Riedel-de Haen Art. No. 34851)

50% formic acid p.a. (for example Fluka Art. No. 09676)

Preparation of the Starting Solution:

At least 1.5 mg of the test substance are weighed out accurately into a wide-mouth 10 mm screw V-vial (from Glastechnik Gräfenroda GmbH, Art. No. 8004-WM-H/V15µ) with fitting screw cap and septum, dimethyl sulphoxide is added to a concentration of 50 mg/ml and the vial is vortexed for 30 minutes.

Preparation of the Calibration Solutions:

The pipetting steps necessary are effected in 1.2 ml 96-well deep well plates (DWPs) (e.g. HJ-Bioanalytik GmbH Art. No. 850289) with the aid of a liquid-handling robot. The solvent used is a mixture of Chromasolv acetonitrile/distilled water 8:2.

Preparation of the starting solution for calibration solutions (stock solution): 833 µl of the solvent mixture are added to 10 µl of the starting solution (concentration=600 µg/ml), and the mixture is homogenized. Two 1:100 dilutions in separate DWPs are prepared from each test substance, and these are homogenized in turn. One of the 1:100 dilutions is used for the preparation of the calibration solutions; the second dilution is used for the optimization of the MS/MS parameters.

Calibration solution 5 (600 ng/ml): 270 µl of the solvent mixture are added to 30 µl of the stock solution, and the mixture is homogenized.

Calibration solution 4 (60 ng/ml): 270 µl of the solvent mixture are added to 30 µl of the calibration solution 5, and the mixture is homogenized.

Calibration solution 3 (12 ng/ml): 400 µl of the solvent mixture are added to 100 µl of the calibration solution 4, and the mixture is homogenized.

Calibration solution 2 (1.2 ng/ml): 270 µl of the solvent mixture are added to 30 µl of the calibration solution 3, and the mixture is homogenized.

Calibration solution 1 (0.6 ng/ml): 150 µl of the solvent mixture are added to 150 µl of the calibration solution 2, and the mixture is homogenized.

Preparation of the Sample Solutions:

The pipetting steps necessary are effected in 1.2 ml 96-well DWPs (e.g. HJ-Bioanalytik GmbH Art. No. 850289) with the aid of a liquid-handling robot.

1000 µl of PBS buffer pH 6.5 are added to 10.1 µl of the stock solution.

Procedure:

The pipetting steps necessary are effected in 1.2 ml 96-well DWPs (e.g. HJ-Bioanalytik GmbH Art. No. 850289) with the aid of a liquid-handling robot.

Using a temperature-adjustable shaker (e.g. Eppendorf Thermomixer comfort Art. No. 5355000.011), the sample solutions prepared in this manner are shaken at 20° C. and 1400 rpm for 24 hours. 180 µl are removed from each of these solutions and transferred into Beckman Polyallomer centrifuge tubes (Art. No. 343621). These solutions are centrifuged at about 223 000×g for 1 hour (e.g. from Beckman Optima L-90K Ultracentrifuge with type 42.2 Ti rotor at 42 000 rpm). 100 µl of the supernatant are removed from each sample solution, and diluted 1:10 and 1:1000 with PBS buffer 6.5.

Analysis:

The samples are analysed by means of HPLC/MS-MS. The test compound is quantified by means of a five-point calibration curve. The solubility is expressed in mg/l. Analysis sequence: 1) blank (solvent mixture); 2) calibration solution 0.6 ng/ml; 3) calibration solution 1.2 ng/ml; 4) calibration solution 12 ng/ml; 5) calibration solution 60 ng/ml; 6) calibration solution 600 ng/ml; 7) blank (solvent mixture); 8) sample solution 1:1000; 7) sample solution 1:10.

HPLC/MS-MS Method

HPLC: Agilent 1100, quat. pump (G1311A), autosampler CTC HTS PAL, degasser (G1322A) and column thermostat (G1316A); column: Oasis HLB 20 mm×2.1 mm, 25µ; temperature: 40° C.; eluent A: water+0.5 ml of formic acid/1; eluent B: acetonitrile+0.5 ml of formic acid/1; flow rate: 2.5 ml/min; stop time 1.5 min; gradient: 0 min 95% A, 5% B; ramp: 0-0.5 min 5% A, 95% B; 0.5-0.84 min 5% A, 95% B; ramp: 0.84-0.85 min 95% A, 5% B; 0.85-1.5 min 95% A, 5% B.

MS/MS: WATERS Quattro Micro Tandem MS/MS; Z-Spray API interface; HPLC-MS inlet splitter 1:20; analysis in the ESI mode.

For each test substance, the instrument parameters are optimized automatically by means of the MassLynx/QuanOptimize software, by injection of the stock solution described above (second 1:100 dilution).

C) Working Examples of Pharmaceutical Compositions

The inventive substances can be converted to pharmaceutical preparations as follows:

Tablet:

Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg, diameter 8 mm, radius of curvature 12 mm

Production:

The mixture of the compound of Example 1, lactose and starch is granulated with a 5% solution (m/m) of the PVP in water. The granules are dried and then mixed with the magnesium stearate for 5 min. This mixture is compressed in a conventional tabletting press (see above for tablet format).

Oral Suspension:

Composition:

1000 mg of the compound of Example 1, 1000 mg of ethanol (96%), 400 mg of Rhodigel (xanthan gum) (from FMC, USA) and 99 g of water.

A single dose of 100 mg of the inventive compound corresponds to 10 ml of oral suspension.

Production:

The Rhodigel is suspended in ethanol, and the compound of Example 1 is added to the suspension. The water is added while stirring. The mixture is stirred for approx. 6 h until the Rhodigel has finished swelling.

Intravenously Administrable Solution:

Composition:

1 mg of the compound of Example 1, 15 g of polyethylene glycol 400 and 250 g of water for injection purposes.

Production:

The compound of Example 1 is dissolved together with polyethylene glycol 400 by stirring in the water. The solution is sterilized by filtration (pore diameter 0.22 µm) and dispensed under aseptic conditions into heat-sterilized infusion bottles. The latter are closed with infusion stoppers and crimped caps.

The invention claimed is:

1. Compound of the formula (I)

in which $R^1$ is a group of the formula where

\* is the attachment site to the heterocycle, $R^6$ is pyrid-2-yl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,2-pyrazol-5-yl, where pyrid-2-yl, pyrimid-2-yl, 1,3-thiazol-2-yl and 1,3-thiazol-4-yl are substituted by 1 to 2 substituents, where the substituents are each independently selected from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_{-1}$-$C_4$-alkylcarbonyl, $C_1$-$C_4$-alkoxycarbonyl, $C_1$-$C_4$-alkylaminocarbonyl and $C_3$-$C_6$-cycloalkylcarbonyl, in which alkyl, alkylamino, alkylcarbonyl, alkylaminocarbonyl and cycloalkylcarbonyl may be substituted by one substituent, where the substituent is selected from the group consisting of halogen, cyano, hydroxyl, amino, trifluoromethyl and $C_3$-$C_6$-cycloalkyl, and where 2-aminopyrimid-4-yl, 2-cyclopropylaminopyrimid-4-yl, 2-methylaminopyrimid-4-yl, 2-ethylaminopyrimid-4-yl and 1,2-pyrazol-5-yl may each be substituted by 1 to 2 substituents, where the substituents are each independently selected from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_{-1}$-$C_4$-alkylcarbonyl, $C_1$-$C_4$-alkoxycarbonyl, $C_1$-$C_4$-alkylaminocarbonyl and $C_3$-$C_6$-cycloalkylcarbonyl, $R^2$ is phenyl, where phenyl may be substituted by 1 to 3 substituents, where the substituents are each independently selected from the group consistinf of hydroxyl, halogen, cyano, trifluoromethyl, trifluoromethoxy, aminocarbonyl, $C_1$-$C_4$-alkyl, $C_1$-$C_4$-alkoxy, $C_1$-$C_4$-alkylamino, $C_1$-$C_4$-alkoxymethyl, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulphonyl, $C_1$-$C_4$-alkylsulphonylamino, $C_1$-$C_4$-alkylaminosulphonyl, phenyl, pyrrolidinyl, piperidinyl, morpholinyl, piperazinyl, pyrrolidinylmethyl, piperidinylmethyl, morpholinylmethyl and piperazinylmethyl, in which phenyl, pyrrolidinyl, piperidinyl, morpholinyl, piperazinyl, pyrrolidinylmethyl, piperidinylmethyl, morpholinylmethyl and piperazinylmethyl may each be substituted by 1 to 3 substituents, where the substituents are each independently selected from the group consisting of halogen, cyano, trifluoromethyl, trifluoromethoxy and $C_1$-$C_4$-alkyl, $R^3$ is hydrogen, halogen, cyano, trifluoromethyl, $C_1$-$C_3$-alkyl or cyclopropyl, either $R^4$ is hydrogen, halogen, cyano, trifluoromethyl, $C_1$-$C_3$-alkyl or cyclopropyl, and $R^5$ is halogen, cyano, trifluoromethyl, hydroxycarbonyl, aminocarbonyl, $C_1$-$C_4$-alkyl, $C_1$-$C_4$-alkoxycarbonyl, $C_1$-$C_4$-alkylaminocarbonyl or 5- or 6-membered heterocyclylcarbonyl, where heterocyclylcarbonyl may be substituted by 1 to 3 substituents, where the substituents are each independently selected from the group consisting of oxo, halogen, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, and where alkylaminocarbonyl may be substituted by one substituent, where the substituent is selected from the group consisting of hydroxyl, amino, hydroxycarbonyl, aminocarbonyl, $C_1$-$C_4$-alkoxy, $C_1$-$C_4$-alkylamino and 5- or 6-membered heterocyclyl, in which heterocyclyl may be substituted by 1 to 2 substituents, where the substituents are each independently selected from the group consisting of oxo, halogen, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, or $R^4$ is halogen, cyano, trifluoromethyl, hydroxycarbonyl, aminocarbonyl, $C_1$-$C_4$-alkyl, $C_1$-$C_4$-alkoxycarbonyl, $C_1$-$C_4$-alkylaminocarbonyl or 5- or 6-membered heterocyclylcarbonyl, where heterocyclylcarbonyl may be substituted by 1 to 3 substituents, where the substituents are each independently selected from the group consisting of oxo, halogen, C₁-C₄-alkyl, C₁-C₄-alkoxy, C₁-C₄-alkylamino, C₁-C₄-alkylcarbonyl, C₁-C₄-alkoxycarbonyl and C₁-C₄-alkylaminocarbonyl, and where alkylaminocarbonyl may be substituted by one substituent, where the substituent is selected from the group consisting of hydroxyl, amino, hydroxycarbonyl, aminocarbonyl, C₁-C₄-alkoxy, C₁-C₄-alkylamino and 5- or 6-membered heterocyclyl,
in which heterocyclyl may be substituted by 1 to 2 substituents, where the substituents are each independently selected from the group consisting of oxo, halogen, C₁-C₄-alkyl, C₁-C₄-alkoxy, C₁-C₄-alkylamino, C₁-C₄-alkylcarbonyl, C₁-C₄-alkoxycarbonyl and C₁-C₄-alkylaminocarbonyl, and R⁵ is hydrogen, halogen, cyano, trifluoromethyl, C₁-C₃-alkyl or cyclopropyl, or one of the salts thereof.

2. The compound according to claim 1, characterized in that

R¹ is a group of the formula

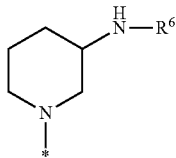

where

* is the attachment site to the heterocycle,

R⁶ is pyrid-2-yl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,2-pyrazol 5-yl, where pyrid-2-yl, pyrimid-2-yl, 1,3-thiazol-2-yl and 1,3-thiazol-4-yl are substituted by 1 to 2 substituents, where the substituents are each independently selected from the group consisting of halogen, cyano, nitro, amino, trifluoromethyl, trifluoromethoxy, aminocarbonyl, trifluoromethylcarbonyl, C₁-C₄-alkyl, C₁-C₄-alkoxy, C₁-C₄-alkylamino, C-₁-C₄-alkylcarbonyl, C₁-C₄-alkoxycarbonyl, C₁-C₄-alkylaminocarbonyl and C₃-C₆-cycloalkylcarbonyl, in which alkyl, alkylamino, alkylcarbonyl, alkylaminocarbonyl and cycloalkylcarbonyl may be substituted by one substituent, where the substituent is selected from the group consisting of halogen, cyano, hydroxyl, amino, trifluoromethyl and C₃-C₆-cycloalkyl, and where 2-aminopyrimid-4-yl, 2-cyclopropylaminopyrimid-4-yl, 2-methylaminopyrimid-4-yl, 2-ethylaminopyrimid-4-yl and 1,2-pyrazol-5-yl may each be substituted by 1 to 2 substituents, where the substituents are each independently selected from the group consisting of halogen, cyano, nitro, amino, trifluoromethyl, trifluoromethoxy, aminocarbonyl, trifluoromethylcarbonyl, C₁-C₄-alkyl, C₁-C₄-alkoxy, C₁-C₄-alkylamino, C -₁-C₄-alkylcarbonyl, C₁-C₄-alkoxycarbonyl, C₁-C₄-alkylaminocarbonyl and C₃-C₆-cycloalkylcarbonyl, R² is phenyl, where phenyl may be substituted by 1 to 3 substituents, where the substituents are each independently selected from the group consisting of chlorine, fluorine, trifluoromethyl, trifluoromethoxy, methyl and methoxy, R³ is hydrogen, either R⁴ is hydrogen, and R⁵ is halogen, cyano, trifluoromethyl, hydroxycarbonyl, aminocarbonyl, C₁-C₄-alkyl, C₁-C₄-alkoxycarbonyl, C₁-C₄-alkylaminocarbonyl or 5- or 6-membered heterocyclylcarbonyl, where heterocyclylcarbonyl may be substituted by 1 to 3 substituents, where the substituents are each independently selected from the group consisting of oxo, halogen, C₁-C₄-alkyl, C₁-C₄-alkoxy, C₁-C₄-alkylamino, C₁-C₄-alkylcarbonyl, C₁-C₄-alkoxycarbonyl and C₁-C₄-alkylaminocarbonyl, and where alkylaminocarbonyl may be substituted by one substituent, where the substituent is selected from the group consisting of hydroxyl, amino, hydroxycarbonyl, aminocarbonyl, C₁-C₄-alkoxy, C₁-C₄-alkylamino and 5- or 6-membered heterocyclyl,
in which heterocyclyl may be substituted by 1 to 2 substituents, where the substituents are each independently selected from the group consisting of oxo, halogen, C₁-C₄-alkyl, C₁-C₄-alkoxy, C₁-C₄-alkylamino, C₁-C₄-alkylcarbonyl, C₁-C₄-alkoxycarbonyl and C₁-C₄-alkylaminocarbonyl, or R⁴ is trifluoromethyl, and R⁵ is cyano, or one of the salts thereof.

3. The compound according to claim 1, characterized in that

R¹ is a group of the formula

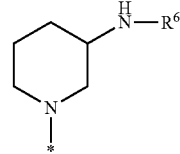

where

* is the attachment site to the heterocycle,

R⁶ is pyrid-2-yl or 1,3-thiazol-2-yl, where pyrid-2-yl and 1,3-thiazol-2-yl are substituted by 1 to 2 substituents, where the substituents are each independently selected from the group consisting of cyano, nitro, amino, trifluoromethylcarbonyl, ethylcarbonyl and methylcarbonyl, R² is phenyl, where phenyl is substituted by 1 or 2 substituents, where the substituents are each independently selected from the group consisting of chlorine, fluorine, trifluoromethyl, trifluoromethoxy, methyl and methoxy, R³ is hydrogen, either R⁴ is hydrogen, and R⁵ is cyano, trifluoromethyl, hydroxycarbonyl, methoxycarbonyl, ethoxycarbonyl, C₁-C₂-alkylaminocarbonyl, piperazinylcarbonyl, piperidinylcarbonyl or morpholinylcarbonyl, where piperazinylcarbonyl, piperidinylcarbonyl and morpholinylcarbonyl may each be substituted by 1 to 3 substituents, where the substituents are each independently selected from the group consisting of oxo, halogen and $C_1$-$C_4$-alkyl, and where alkylaminocarbonyl may be substituted by one substituent, where the substituent is selected from the group consisting of piperazinyl, piperidinyl and morpholinyl, where piperazinyl, piperidinyl and morpholinyl may each be substituted by 1 to 2 substituents, where the substituents are each independently selected from the group consisting of oxo, halogen and $C_1$-$C_4$-alkyl, or $R^4$ is trifluoromethyl, and $R^5$ is cyano, or one of the salts thereof.

4. The compound according to claim 1, characterized in that $R^1$ is a group of the formula

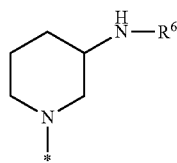

where

* is the attachment site to the heterocycle, $R^6$ is a group of the formula

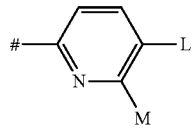

where # is the attachment site to NH, either

L is cyano, and

M is hydrogen, or

L is cyano, nitro or trifluoromethylcarbonyl, and

M is amino, $R^2$ is phenyl, where phenyl is substituted by 1 or 2 substituents, where the substituents are each independently selected from the group consisting of chlorine, fluorine and methoxy, $R^3$ is hydrogen, either $R^4$ is hydrogen, and $R^5$ is cyano, hydroxycarbonyl, methoxycarbonyl, methylaminocarbonyl, dimethylaminocarbonyl, piperazinylcarbonyl or piperidinylcarbonyl, where piperazinylcarbonyl and piperidinylcarbonyl are each substituted by 1 to 2 substituents, where the substituents are each independently selected from the group consisting of halogen and $C_1$-$C_4$-alkyl, and where methylaminocarbonyl and dimethylaminocarbonyl are substituted by one piperidinyl substituent, in which piperidinyl is substituted by 1 to 2 substituents, where the substituents are each independently selected from the group consisting of halogen and $C_1$-$C_4$-alkyl, or $R^4$ is trifluoromethyl, and $R^5$ is cyano, or one of the salts thereof.

5. A process for preparing the compound of formula (I) or one of the salts thereof, solvates thereof or solvates of the salts thereof according to claim 1, characterized in that either

[A] a compound of the formula

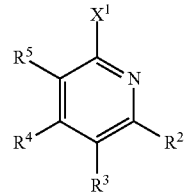

(II)

in which $R^2$, $R^3$, $R^4$ and $R^5$ are each as defined in claim 1, and $X^1$ is halogen, preferably chlorine or fluorine, is reacted with a compound of the formula $$R^1\text{—H} \qquad (III)$$

in which $R^1$ is as defined in claim 1 or

[B] a compound of the formula

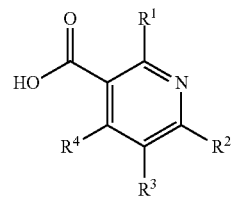

(Ia)

in which $R^1$, $R^2$, $R^3$ and $R^4$ are each as defined in claim 1, is reacted with a compound of the formula $$R^{5a}\text{—H} \qquad (IV)$$

in which $R^{5a}$ is $C_1$-$C_4$-alkoxy, $C_1$-$C_4$-alkylamino or 5- to 6-membered heterocyclyl, where heterocyclyl may be substituted by 1 to 3 substituents, where the substituents are each independently selected from the group consisting of oxo, halogen, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, and where alkylamino may be substituted by one substituent, where the substituent is selected from the group consisting of hydroxyl, amino, hydroxycarbonyl, aminocarbonyl, $C_1$-$C_4$-alkoxy, $C_1$-$C_4$-alkylamino and 5- or 6-membered heterocyclyl, in which heterocyclyl may be substituted by 1 to 2 substituents, where the substituents are each independently selected from the group consisting of oxo, halogen, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, to give a compound of the formula (Ib)

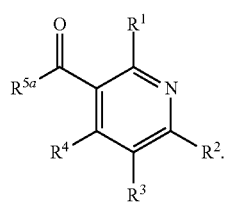

6. A pharmaceutical composition comprising a compound according to claim 1 in combination with an inert, nontoxic, pharmaceutically suitable excipient.

7. A method of treating a haematological disorder selected from leucopenia and neutropenia in a human or animal comprising administering a therapeutically effective amount of the compound according to claim 1 to the human or animal.

8. A method of ex vivo propagation of adult haematopoietic stem cells from at least one of the group consisting of bone marrow and peripheral blood, or for ex vivo propagation of embryonic stem cells from umbilical cord blood, wherein an effective amount of the compound according to claim 1 is added to increase a rate of proliferation of the haematopoietic stem cells.

* * * * *